(12) United States Patent
Anslyn et al.

(10) Patent No.: US 7,670,847 B2
(45) Date of Patent: *Mar. 2, 2010

(54) DETERMINING ENANTIOMERIC EXCESS USING INDICATOR-DISPLACEMENT ASSAYS

(75) Inventors: Eric V. Anslyn, Austin, TX (US); Jan Frantz Folmer-Andersen, Austin, TX (US); Lei Zhu, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/839,085

(22) Filed: Aug. 15, 2007

(65) Prior Publication Data

US 2007/0292968 A1    Dec. 20, 2007

Related U.S. Application Data

(63) Continuation of application No. 11/036,642, filed on Jan. 14, 2005.

(60) Provisional application No. 60/537,104, filed on Jan. 16, 2004.

(51) Int. Cl.
*G01N 21/00* (2006.01)
*G01N 33/00* (2006.01)
*B01D 15/08* (2006.01)

(52) U.S. Cl. .................. 436/164; 436/86; 435/7.92; 435/7.93; 564/424

(58) Field of Classification Search .................. 436/164, 436/86; 564/424; 435/7.92, 7.93
See application file for complete search history.

(56) References Cited

U.S. PATENT DOCUMENTS

6,265,615 B1 * 7/2001 Kaner et al. ............... 564/424

OTHER PUBLICATIONS

Itoh et al., Stereoselectivity and Enantiomer-Enantiomer Interactions in the Binding of Ibuprofen to Human Serum Albumin, 1997, Wiley Liss, Inc., v. 9, p. 643-649.*

Toyo'oka, Recent Progress in Liquid Chromatographic Enantioseparation Based Upon Diastereomer Formation with Fluorescent Chiral Derivatization Reagents, 1996, John Wiley & Sons, Ltd., v. 10, p. 265-277.*

Wiskur, S. L.; et al., "Thermodynamic Analysis of Receptors Based on Guanidinium/Boronic Acid Groups for the Complexation of Carboxylates, α-Hydroxycarboxylates, and Diols: Driving Force for Binding and Cooperativity", *Chemistry* 10, pp. 3792-3804, 2004.

(Continued)

*Primary Examiner*—Jill Warden
*Assistant Examiner*—Lore Jarrett
(74) *Attorney, Agent, or Firm*—Baker Botts L.L.P.

(57) ABSTRACT

The invention includes an enantioselective indicator-displacement assay useful to determine enantiomeric excess (ee) enantiomeric samples colorimetrically. Determination may be by inspection of color with the naked eye, spectrographic measurement, or mathematical calculation. Concentration may also be determined. The assay may involve two independent absorption measurements. On suitable group of enantiomeric molecules to be assayed include α-hydroxy acids. The inherent relationship between the absorbance of the indicator-displacement ensemble and the overall concentration and ee of the analyte is established through solution equilibria. The invention also includes use of the assay in drug screening and manufacturing, high throughput screening of catalysts and kits for use in conducting assays of the invention.

12 Claims, 31 Drawing Sheets

OTHER PUBLICATIONS

Ahn, K. H. et al., "Fluorescence Sensing of Ammonium and Organoammonium Ions with Tripodal Oxazoline Receptors", *Org. Lett.* 5, pp. 1419-1422, Jan. 9, 2003.

Fabbrizzi, L. et al., "The Design of Fluorescent Sensors for Anions: Taking Profit from the Metal-Ligand Interaction and Exploiting Two Distinct Paradigms", *Dalton Trans.* pp. 3471-3479, 2003.

Stambuli, J. P. et al., "Recent Advances in the Discovery of Organometallic Catalysts using High-Throughput Screening Assays", *Curr. Opin. Chem. Biol.*, 7, pp. 420-426, 2003.

Tobey, S. L. et al., "Determination of Inorganic PHosphate in Serum and Saliva using a Synthetic Receptor", *Organic Letters*, vol. 5, No. 12, pp. 2029-2031, 2003.

Zhong, Z. et al., "Controlling the Oxygenation Level of Hemoglobin by using a Synthetic Receptor for 2,3-Bisphosphoglycerate", *Angewandte Chemie Int. Ed.*, 42, pp. 3005-3008, 2003.

Fabbrizzi, L. et al., "Pyrophosphate Detection in Water by Fluorescence Competition Assays: Inducing Selectivity through the Choice of the Indicator", *Angewandte Chemie Int. Ed.* vol. 41, No. 20, pp. 3811-3814, 2002.

Finn, M. G., "Emergin Methods for the Rapid Determination of Enantiomeric Excess", *Chirality*, 14, pp. 534-540, 2002.

Holmes, A. E., et al., "Systhesis and Circular Dichroism Studies of N,N-Bis(2-quinolylmenthyl)amino Acid CU(II), Complexes: Determination of Absolute Configuration and Enantiomeric Excess by the Exciton Coupling Method", *Chirality*, 14, pp. 471-477, 2002.

Lee, S. J., et al., "A Chiral Molecular Square with Metalo-Corners for Enantioselective Sensing", *Am. Chem. Soc.*, 124, pp. 4554-4555, 2002.

Lin, J., et al., "Bisbinaphythyl Macrocycle-Based Highly Enantioselective Fluorescent Sensors for α-Hydroxycarboxylic Acids", *Org. Lett.*, 4, pp. 3297-3300, 2002.

Taran, F. et al., "High-Throughput Screening of Enantioselective Catalysts by Immunoassay", *Angew. Chem. Int. Ed.*, 41, pp. 124-127, 2002.

Tsukamoto, M. et al., "Recent Advances in the Measurement of Enantiomeric Excesses", *Adv. Synth. Catal.*, 344, pp. 453-463, 2002.

van Delden, R. A. et al., "Colour Indicator for Enantiomeric Excess and Assignment of the Configuration of the Major Enantiomer of an Amino Acid Ester", *Chem. Commun.*, pp. 174-175, 2002.

Zhong, Z. et al., "A Colorimetric Sensing Ensemble for Heparin", *J. Am. Chem. Soc.* 124, pp. 9014-9015, 2002.

Beer, G. et al., "Chiral Discrimination wiht a Fluorescent Boron-Dipyrromethene Dye", *J. Chem. Commun.*, pp. 1138-1139, 2001.

Korbel, G. A. et al., "Reaction Microarrays: A Method for Repidly Determinging the Enantiomeric Excess of Thousands of Samples", *Am. Chem. Soc.*, 123, pp. 363.361, 2001.

Reetz, M.T., "Combinatorial and Evolution-Based Methods in the Creation of Enantioselective Catalysts", *Angew. Chem. Int. Ed.*, 40, pp. 284-310, 2001.

Tsubaki, K. et al., "Visual Recognition of Triamines by Phenolphthalein Derivatives: Consideration of the Structure of the Colored Complex", *Organic Letters*, 3, pp. 4067-4069, 2001.

van Delden, R. A. et al., "Color Indicators of Molecular Chirality Based on Doped Liquid Crystals", *Angew. Chem. Int. Ed.*, 40, pp. 3198-3200, 2001.

Wahler, D. et al., "High-throughput Screening for Biocatalysts", *Curr. Opin. Biotechnol.* 12, pp. 535-544, 2001.

Wiskur, S. L. et al., "Teaching Old Indicators New Tricks", *Acc. Chem. Res.* vol. 34, No. 12, pp. 963-972, 2001.

Wiskur, S. L. et al., "Using a Synthetic Receptor to Create an Optical-Sensing Ensemble for a Class of Analytes: A Colorimetric Assay for the Aging of Scotch", *J. Am. Chem. Soc.* 123, pp. 10109-10110, 2001.

Yashima, E. et al., "Switching of a Macromolecular Helicity for Visual Distinction of Molecular Recognition Events" *J. Am. Chem. Soc.* 123, pp. 8159-9160, 2001.

Pugh, V. J. et al., "The First Dendrimer-Based Enantioselective Fluorscent Sensor for the Recognition of Chiral Amino Alcohols", *Angew. Chem. Int. Ed.*, 39, pp. 3638-3641, 2000.

Klein, G. et al., "Enantioselective Fluorogenic Assay of Acetate Hydrolysis for Detecting Lipase Catalytic Antibodies", *Helv. Chim. Acta*, 82, pp. 400-407, 1999.

Lavigne, J. J., et al., "Teaching Old Indicators New Tricks: A Colorimetric Chemosensing Ensemble for Tartrate/Malate in Beverages", *Angew. Chem. Int. Ed.* 38, pp. 3666-3669, 1999.

Kubo, Y. et al., "Colorimetric Chiral Recognition by a Molecular Sensor" *Nature*, 382, pp. 522-524, 1996.

Ramanjulu, J. M. et al., "N-Alkylation of Amino Acid Esters using Sodium Triacetoxyborohydride" *Syn. Commun.*, 26, pp. 1379-1384, 1996.

Burgess, K. et al., "A Reagent for Determining Optical Purities of Diols by Formation of Diasteromeric Arylboronate Esters", *Angew. Chem. Int. Ed. Engl.*, 33, pp. 1182-1184, 1994.

Anslyn, E.V. Presentation at the 'NSF Young Supramolecular Chemistry Symposium' held of Sanibel Island, Florida., 3 pages, Jan. 15, 2004.

McMurry, John; "Organic Chemistry"; Wadsworth, Inc., Brooks/Cole Publishing Co.; pp. 236-239, 1984.

* cited by examiner

DETERMINING ENANTIOMERIC EXCESS USING INDICATOR-DISPLACEMENT ASSAYS

RELATED PATENT APPLICATION

This application is a Continuation of U.S. patent application Ser. No. 11/036,642 filed Jan. 14, 2005, entitled "Determining Enantiomeric Excess Using Indicator-Displacement Assays", which claims the benefit of U.S. Provisional Application No. 60/537,104 filed Jan. 16, 2004.

STATEMENT OF GOVERNMENT INTEREST

The present invention or aspects thereof were invented in whole or in part using funding provided by the National Institutes of Health, Grant GM57306. The U.S. Government may have certain rights in the invention.

FIELD OF THE INVENTION

The invention relates to methods and compositions for determining enantiomeric excess of an analyte. More specifically, the present invention relates to indicator displacement assays to determine the enantiomeric excess of a chiral analyte. The concentration of the analyte may be determined simultaneously.

BACKGROUND

Competitive binding assays are established analytical methods in medicinal and clinical chemistry. A typical competitive binding assay constitutes a receptor and a signaling unit that also serves as a surrogate substrate. The signaling unit possesses an easily observable and quantifiable property, which is modulated in response to competitive binding with an analyte. For instance, modulation of absorbance or emission, or the ability to catalyze a reaction, are common approaches. When the signaling unit is a pH or solvatochromic indicator, the assay is specifically called an indicator-displacement assay.

The advantages of an indicator-displacement assay include: 1) the need to covalently incorporate the chromophore or fluorophore into the structures of receptors or analytes is eliminated; 2) the indicators are exchangeable; 3) the detection mechanism is not directly perturbed by the analyte structures; and 4) secondary tuning of sensitivity and selectivity is available because of the participation of the indicator. The usual molecular recognition driving forces are exploited in constructing successful indicator-displacement assays. So far, assays utilizing ion pairing, hydrogen bonding, reversible covalent interactions, metal coordination, and combinations of these, have been documented. Many physiologically and environmentally important targets, such as phosphate, pyrophosphate, citrate, carbonate, amino acids, etc., can now be detected and quantified through indicator-displacement assays. Despite the successes, the available applications of indicator-displacement assays have been limited to sensing the identity and quantity of given analytes. Indicator-displacement assays have been used in a number of sensing applications, but not in quantification of enantiomeric excess (ee) of a chiral analyte.

However, there is a growing demand for methods of ee determination. For example, the FDA currently requires that pharmaceutical companies create enantiomerically pure substances, or that the enantiomer of the drug be thoroughly studied and found to have no adverse side effects. The synthesis of enantiomerically pure substances requires the use of reagents that produce an enantiomeric excess (ee) of the desired drug enantiomer or its chemical precursor. High throughput screening for such enantioselective reagents entails product-analyzing assays for rapid determination of both the yields and ees from given catalytic reactions. This double-parameter requirement increases the difficulty of assay design. Traditional enantioselective optical chemosensors, such as BINOL based compounds (−)-6 and 7 in FIG. 10, usually rely upon cumbersome empirical ee calibration curves against absorbance or fluorescence intensity for each total concentration of the chiral analyte. Thus a need exists for assays capable of rapidly and accurately determining the concentrations and ees of chiral samples.

SUMMARY OF THE INVENTION

The present invention relates to methods and compositions for analyzing chiral samples with unknown concentrations and enantiomeric excesses using enantioselective indicator-displacement assays. These assays may be applied to analysis of samples comprising α-hydroxycarboxylates, vicinal diols, and amino acids. Without being limited to any particular mechanism of action, the chemical basis for the assays may be the enantioselective, reversible covalent associations between chiral boronic acid receptors and chiral analytes. In addition, metal coordination may be used as the primary associative interaction. In some embodiments of the invention, colorimetric or fluorescent indicators may constitute the reporting module of the assays, and act as secondary tuning units for the enantioselectivity (chiral resolution) and sensitivity of the assays. Specifically, fluorescent indicator 4-methylesculetin (ML) and colorimetric indicators pyrocatechol violet (PV) and alizarin complexone (AC) may provide a broad dynamic range where the enantioselective indicator displacement assays are effective in analyzing chiral α-hydroxyacid and diol samples.

In some embodiments of the invention, a mathematical analysis may be applied to the displacement system to enable the rapid concurrent determinations of the aforementioned two parameters. An iterative curve fitting program was created according to the teachings of the invention. This program enabled the determination of association constants between a chiral receptor and its enantiomeric substrates by iterative fitting of absorbance (or fluorescence intensity) vs. ee curves with the commercial software Origin. The invention contemplates the use of a plurality of approaches to determine association constants between receptors and analytes including, without limitation, (a) traditional competitive binding method, (b) iterative fitting of competitive binding curves with enantiomeric pure analytes, and (c) iterative fitting of A (or F) vs. ee curves at fixed total concentrations, respectively. In some nonlimiting embodiments of the invention, iterative fitting of A (or F) vs. ee curves at fixed total concentrations may be best suited for the unknown chiral sample analysis.

Some assays of the present invention may be faster, simpler, and more economical than present screening assays, such as HPLC. Further they may not require substrate derivatization because they rely on the simple analytical technique of absorption spectroscopy. Additionally, the production of chiral receptors does not require lengthy syntheses. Finally, the mathematical analysis used may eliminate the need for empirical ee calibration curves for each analyte concentration.

BRIEF DESCRIPTION OF THE DRAWINGS

The patent application file contains at least one drawing executed in color. Copies of this patent or patent application publication with color drawing(s) will be provided by the United States Patent and Trademark Office upon request and payment of the necessary fee. Specific embodiments of the present invention are further described in the following detailed description taken in conjunction with the accompanying drawings.

DETAILED DESCRIPTION

Figure 1:
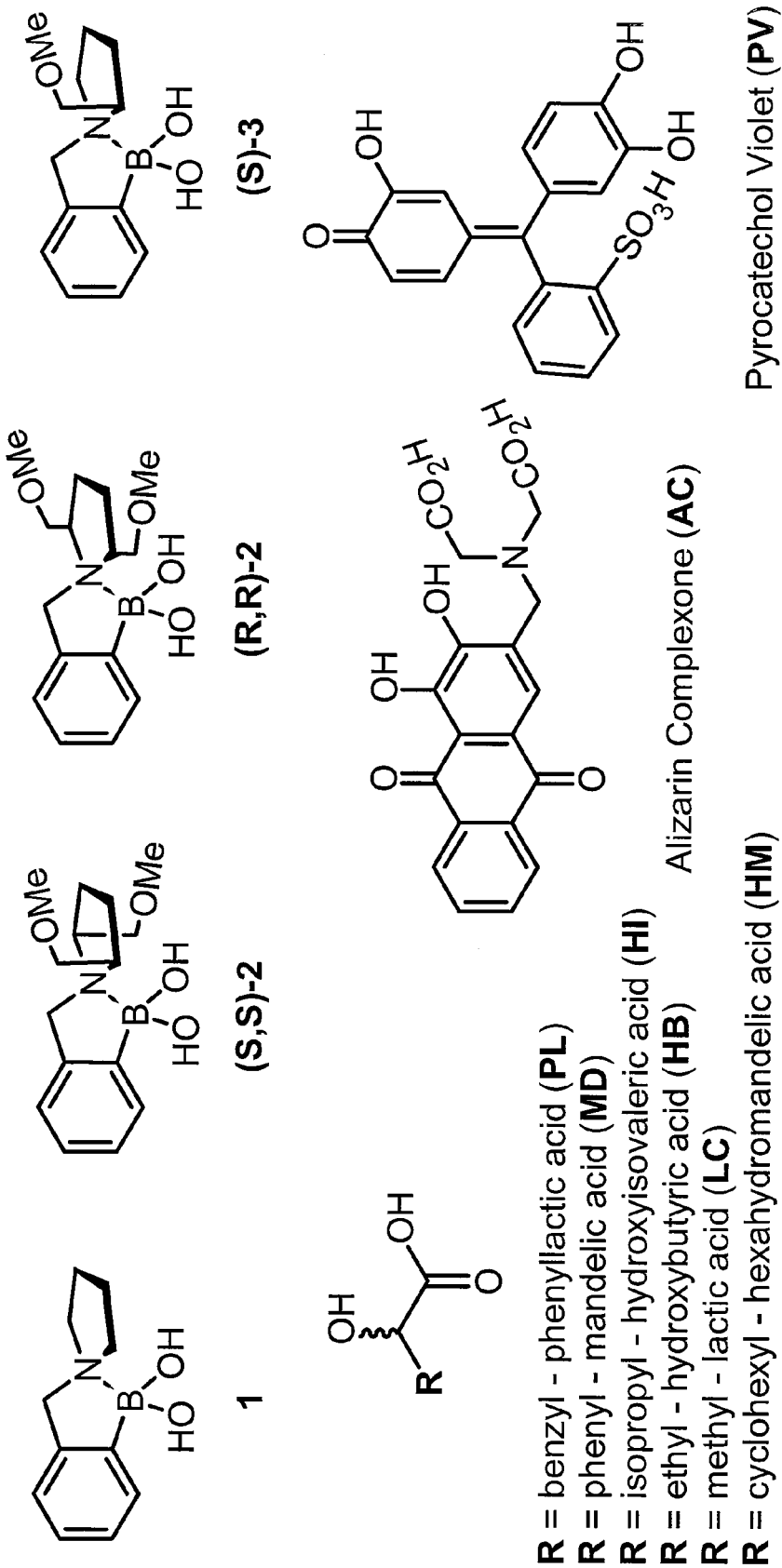
FIG. 1 illustrates chemical structures of various compounds that may be used in connection with specific embodiments of the present invention.

Using assays of the present invention, the ee of an analyte may be determined by visible absorption changes. More specifically, a chiral receptor that differentially binds each enantiomer of an organic molecule may be used. An indicator may be added that also binds the receptor, but is displaced by the analyte. The degree of displacement of the indicator from the receptor differs for each enantiomer of the analyte. Thus, the relative amount of each enantiomer may be determined by measuring either the amount of receptor-bound indicator or the amount of free indicator.

In some embodiments, color differences may be observed by the naked eye in order to ascertain an appropriate amount of enantiomeric excess. Such assays may be useful where it is desirable to use lower level technicians, where rapid determinations are needed, or where it is desirable to limit laboratory equipment expenses. For example, such assay may be useful in drug manufacturing quality control.

In some embodiments, the assay may result in a color change that allows simple visual determination of enantiomeric excess. Such embodiments may be particularly useful in drug manufacturing quality control and obtaining FDA approval of a drug.

In some embodiments, enantiomeric excess may be measured spectroscopically to determine actual excess more precisely. Direct measurements may be used in further mathematical calculations. These mathematical calculations may allow direct correlation of absorbance to ee.

In some embodiments, enantiomeric excess may be measured by nuclear magnetic resonance imaging.

In a specific embodiment, concentration and ee may be determined in the same assay by a two-step analysis utilizing an achiral receptor and a chiral receptor in sequential indicator-displacement assays. Alternatively, concentration and ee may be determined in one measurement using a two-chambered cuvette having a chiral receptor and indicator in one chamber and an achiral receptor and a different indicator in the other chamber. The absorbance of the cuvette is measured at a wavelength corresponding to the isosbestic point of the solutions.

The invention additionally includes the use of ee determination methods in high throughput screening of catalysts and in the analysis of drugs or drug-producing chemical reactions during research or manufacture. During drug manufacture or manufacture of other enantiomerically biased compositions, assays of the present invention may be used to measure ee in a precursor rather than the final product In an exemplary embodiment empirical ee calibration curves may not be required for different analyte concentrations. Since the requirement for different calibration curves is a serious limitation of present methods, the methods of the invention advantageously may provide a simpler, faster, and cheaper way to determine ee.

The invention additionally includes the use of ee determination methods in high throughput screening of catalysts and in the analysis of drugs or drug-producing chemical reactions during research or manufacture. In the context of drug screening, assays of the present invention may be used to reduce the screening time of drugs, reduce the cost of drug development, expedite steps in the FDA approval process, and reduce human errors in drug screening.

According to some embodiments of the invention, indicator displacement and enantioselective indicator-displacement assays may be described as follows:

Scheme 1.

Indicator-Displacement Assay:

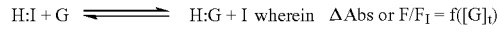

H:I + G ⇌ H:G + I wherein ΔAbs or F/F$_I$ = f([G]$_t$)

Enantioselective Indicator-Displacement Assay:

H*:I + G$_R$ ⇌ H*:G$_R$ + I or

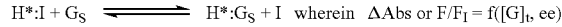

H*:I + G$_S$ ⇌ H*:G$_S$ + I wherein ΔAbs or F/F$_I$ = f([G]$_t$, ee)

H—Host/Receptor; H*—Chiral host/receptor; I—Indicator; G, G$_R$, G$_S$—Guest/Analyte; ΔAbs—Absorbance change; F—fluorescence intensity; F$_I$—fluorescence intensity of an unbound indicator, a constant; [G]$_t$—Total guest concentration; ee—Enantiomeric excess. In the enantioselective indicator-displacement assay, two enantiomers (G$_R$ and G$_S$) in a chiral sample are competing for a fixed amount of receptor/indicator complex (H*:I).

Figure 3:
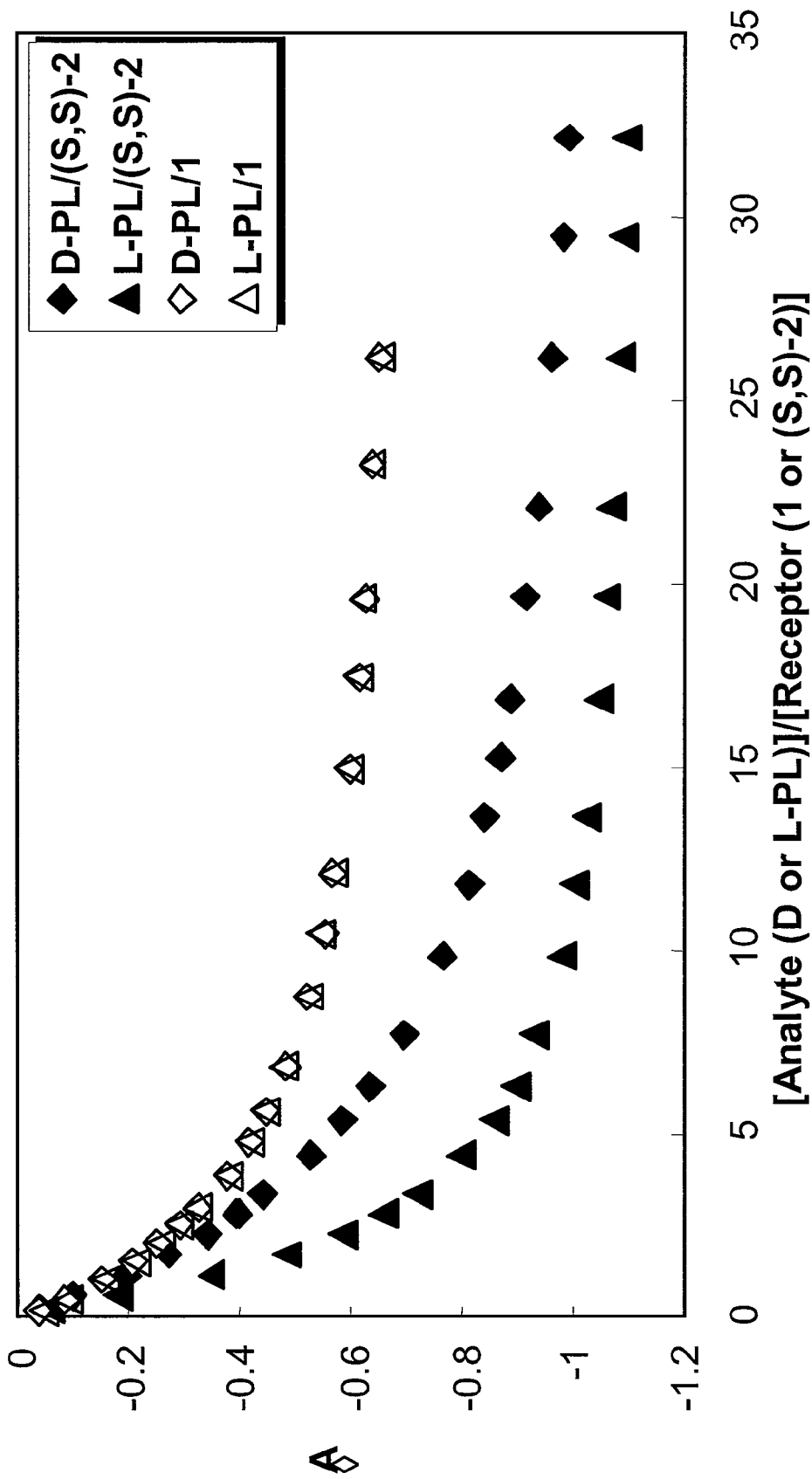
FIG. 3 presents graphically the absorbance change at 520 nm of PV (149 µM) and receptors Compound (S,S)-2 (0.510 mM), or Compound 1 (0.575 mM) in a default buffer with increasing concentration of D- or L-PL (analytes).

In an exemplary embodiment, the present invention exploits the binding of boronic acids to α-hydroxyacids and catechols in aqueous media. For example, the affinity between Compound 1 and phenyllactic acid (PL) (FIG. 1) was determined to be 1.3×10$^3$ M$^{-1}$ (Table 1) using an indicator-displacement assay with the catechol-containing indicators pyrocatechol violet (PV) and alizarin complexone (AC) (FIG. 1). As expected, the achiral receptor Compound 1 (FIG. 1) bound both enantiomers of PL with identical affinities (FIG. 3). Therefore, the total concentration of an unknown PL sample may be determined through an indicator-displacement assay using Compound 1.

Figure 2:
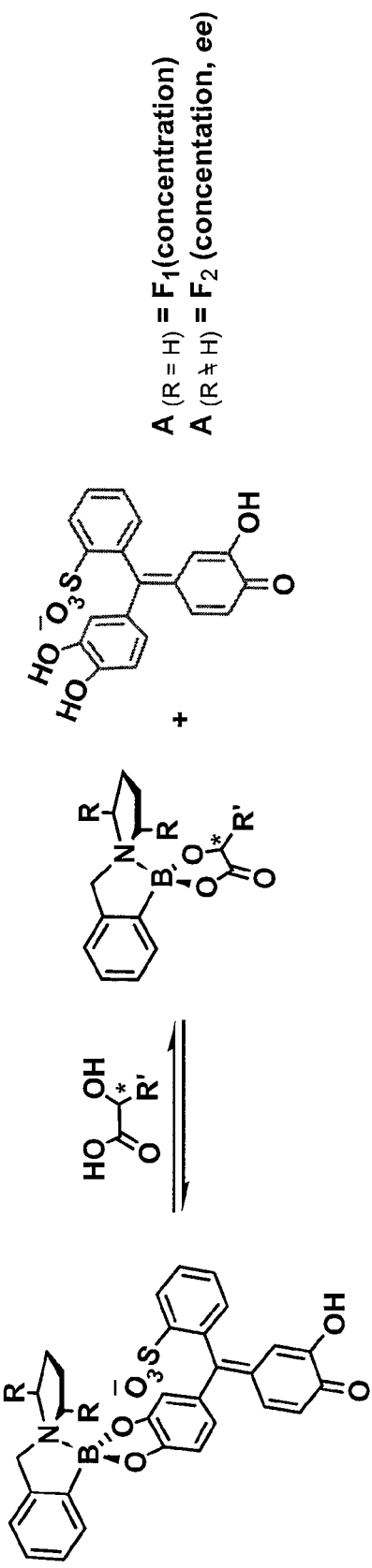
FIG. 2 illustrates a general reaction using pyrocatechol violet and a boronic acid receptor to determine the concentration or the concentration and ee according to the teachings of the present invention.

The general reaction used to determine ee and concentration in some embodiments may be as shown in FIG. 2. By incorporating chirality into the receptor structure, the displacement of the indicator by chiral analytes is enantioselective. This has been confirmed by the binding of chiral receptors (Compounds 2 & 3). D/L-PL was studied using an indicator-displacement assay also. All of these receptors showed comparable affinities (Table 1) to α-hydroxyacids used and PV or AC. Compound (S,S)-2 showed 2.8 times larger affinity to L-PL over D-PL (FIG. 3), while compound (R,R)-2 favored D-PL to the same extent (Table 1). Compound (S)-3, which has one less stereogenic center, displayed less discriminating power between D/L-PL. The association between (S,S)-2 and other α-hydroxyacids were also studied (Table 2) and samples with R-configurations were generally favored (with the exception of lactic acid (LC)).

TABLE 1

Association constants (K$_f$/10$^3$ M$^{-1}$) of boronic receptors (Compounds 1-3) with indicators (PV, AC) and D/L-phenyllactic acids (PL).[a]

| | 1 | (S,S)-2 | (R,R)-2 | (S)-3 |
|---|---|---|---|---|
| PV | 2.3 | 13 | 11 | 15 |
| AC | 13 | 63 | 61 | 57 |
| D-PL | 1.3 | 3.4 | 8.3 | 1.8 |
| L-PL | 1.3 | 9.6 | 3.3 | 2.5 |

[a]Measured by competitive spectrophotometry in 75% (v/v) methanolic aqueous solution buffered with 10 mM HEPES at pH 7.4 (default buffer), data with PV or AC were taken at 520 nm and 536 nm respectively.

TABLE 2

Association constants (K$_R$, K$_S$) between Compound (S,S)-2 and α-hydroxyacid substrates.[a]

| | PL | MD | HI | HB | LC | HM |
|---|---|---|---|---|---|---|
| K$_R$/(10$^3$ M$^{-1}$) | 3.4 | 2.0 | 4.2 | 3.2 | 4.5 | 4.3 |
| K$_S$/(10$^3$ M$^{-1}$) | 9.6 | 3.0 | 5.9 | 4.2 | 4.3 | 5.5 |

[a]Measured as stated in Table 1. K$_R$ and K$_S$ are association constants for R- and S-configured α-hydroxyacids respectively.

Figure 4:
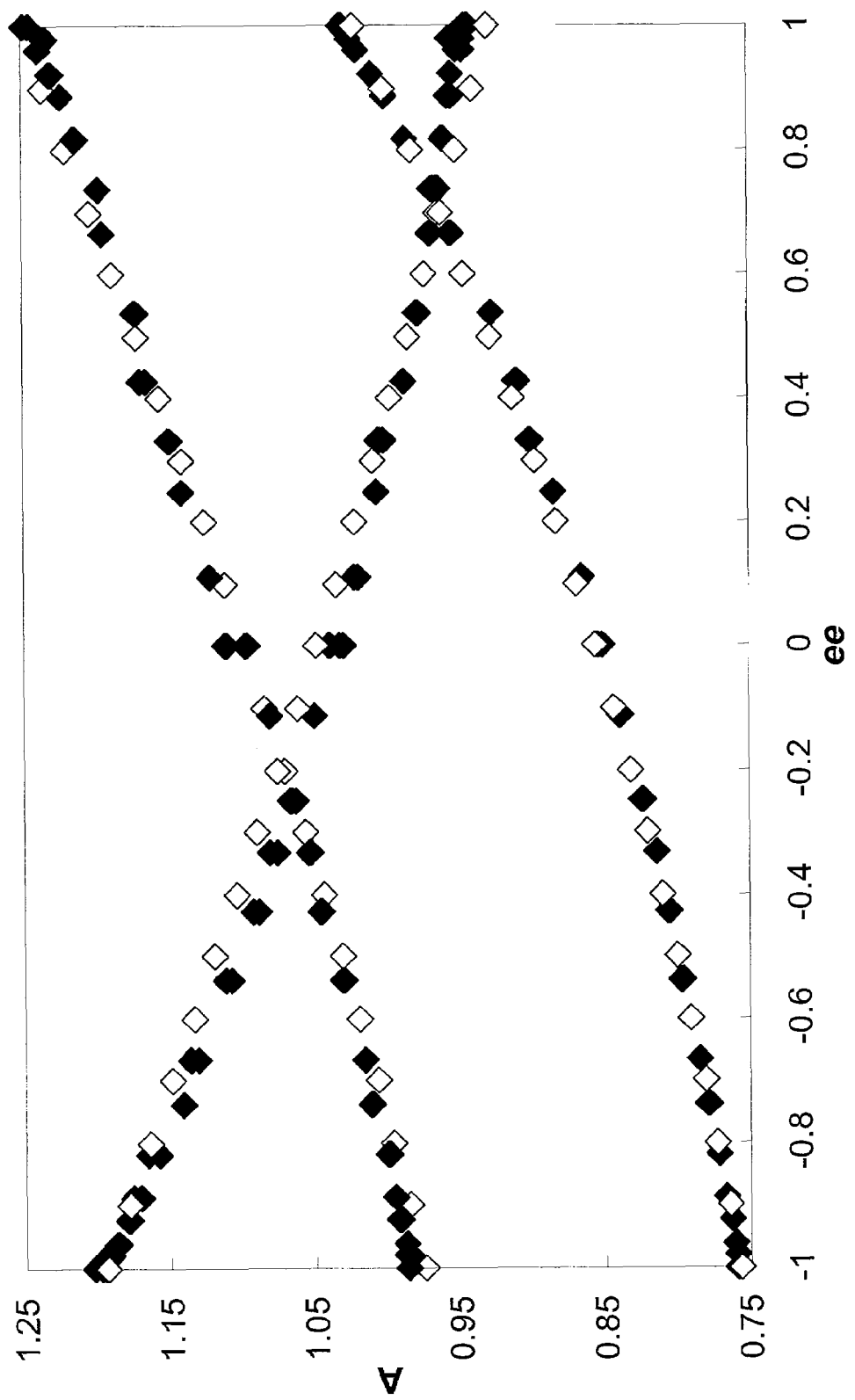
FIG. 4 presents graphically the absorbance change at 520 nm of PV, receptor, and analyte solutions upon increasing ee of D-PL. Black diamonds: $I_t=149$ µM, $H_t$ [Compound (S,S)-2]=0.51 mM, $G_t=1.50$ mM; Blue diamonds: $I_t=149$ µM, $H_t$ [Compound (S,S)-2]=0.51 mM, $G_t=3.00$ mM; Red diamonds: $I_t=141$ mM,[9] $H_t$ [Compound (R,R)-2]=0.52 mM, $G_t=1.50$ mM. Open diamonds: calculated data.

When monitoring the absorbance (520 nm) of the receptor-indicator complex, the different displacement profiles by D/L-PL dictate that at a given concentration, the enantiomeric samples have distinct UV absorbances. The difference (ΔΔA) can be as large as 0.27. An A vs. ee correlation at 1.5 mM analyte concentration was determined (FIG. 4). The absorbance of the sample increased (filled black diamond) when the percentage of stronger binding enantiomer (L-PL) was decreased because of less competitive binding. When the total analyte concentration was adjusted to 3.0 mM, the overall absorption of this series of samples (blue diamond) decreased due to more efficient displacement of the indicator; while the relative correlation between A and ee remained unchanged. When receptor Compound (S,S)-2 was replaced by its enantiomer Compound (R,R)-2 at a slightly different concentration, a near-mirror image A-ee correlation (red) was observed. The A-ee relationships were found to be curved (FIG. 4) where the change in absorbance was slightly, but consistently greater. This likely occurs because the stronger binding enantiomer is more dominant in the overall signal modulation. Because the behavior of all the species obey solution equilibria, the absorbance change through the variation of solution composition may be mathematically modeled.

In one mathematical model, four interacting substances (indicator I, chiral receptor H, two enantiomers of the analyte G$_R$/G$_S$) are present in solution. Their solution species concentrations are interdependent through three equilibria: [HG$_R$]=K$_R$[G$_R$][H], [HG$_S$]=K$_S$[G$_S$][H], and [HI]=K$_I$[I][H]. These concentrations are related by three mass balances: [I]+[HI]=I$_t$, [G$_R$]+[G$_S$]+[HG$_R$]+[HG$_S$]=G$_t$, and [H]+[HI]+[HG$_R$]+[HG$_S$]=H$_t$. The absorbance of the sample is given by Beer's Law (Eq. 1), $$A = \epsilon_I b[I] + \epsilon_{HI} b[HI] \quad \text{(Eq. 1)}$$

and ee is defined in the terms of analyte concentrations (Eq. 2).

$$ee_R = \frac{([G_R] + [HG_R]) - ([G_S] + [HG_S])}{G_t} \quad (Eq.\ 2)$$

The total of eight equations are mathematically transformed to produce Eq. 3.

$$\frac{A - \varepsilon_I b I_t}{b \Delta \varepsilon} + \frac{\varepsilon_I b I_t - A}{K_I(A - \varepsilon_{HI} b I_t)} + \frac{K_R G_t (1 + ee_R)(\varepsilon_I b I_t - A)}{2[A(K_I - K_R) - b I_t(\varepsilon_{HI} K_I - \varepsilon_I K_R)]} + \frac{K_S G_t (1 - ee_R)(\varepsilon_I b I_t - A)}{2[A(K_I - K_S) - b I_t(\varepsilon_{HI} K_I - \varepsilon_I K_S)]} = H_t \quad (Eq.\ 3)$$

Parameters $\varepsilon_I$, $\varepsilon_{HI}$ and $K_I$ are determined from a receptor/indicator isotherm, $K_R$ and $K_S$ from an indicator-displacement assay, $I_t$ and $H_t$ are gravimetrically determined, and the analyte total concentration $G_t$ is obtained from an indicator-displacement assay with achiral receptor Compound 1 as previously described. Therefore, there are only two variables—A and ee—in Eq. 3. Eq. 3 may be further mathematically transformed into the standard polynomial format $PA^4 + QA^3 + RA^2 + SA + T = 0$ with the aid of the commercial software Mathematica®, where P, Q, R, S, T are all functions of ee. Therefore, by solving the 4$^{th}$ order polynomial equation, the absorbance of the displacement cocktail is successfully correlated to the ee of the analyte. The eight experimentally determined constants ($\varepsilon_I$, $\varepsilon_{HI}$, $K_I$, $K_R$, $K_S$, $I_t$, $H_t$ and $G_t$) are input into Eq. 3 to generate theoretical data. When applied to the α-hydroxyacid embodiment described above, theoretical data (open diamonds in FIG. 3) correlates well with the actual observations.

The indicator-displacement embodiment described above may be used to determine the concentration and ee of an α-hydroxyacid sample by carrying out two independent measurements. First, the absorbance spectrum from an indicator-displacement assay containing the achiral receptor (Compound 1) and PV may be measured to obtain the overall concentration of the α-hydroxyacid. Second, another absorbance reading with a chiral ensemble (Compound (S,S)-2 and PV) may be used in Eq. 3 to quantify the ee of the sample. This may be performed without generating an empirical ee calibration curve for the determined analyte concentration. The effectiveness of this assay is shown in Table 3, where the total concentration and ee of three PL samples were determined.[10] The accuracy of the overall concentration was ±10% whereas the ee could be determined within ±20% error.

TABLE 3

Determination of concentration and ee of unknown phenyllactic acid (PL) samples.

| | Concentration (Actual)/mM | Concentration (Determined)/mM | ee (Actual) | ee (Determined) |
|---|---|---|---|---|
| 1 | 20.0 | 21.5 | 1.00 | 0.98 |
| 2 | 26.5 | 28.1 | −0.89 | −0.71 |
| 3 | 28.5 | 31.4 | −0.82 | −0.68 |

Aromatic boronic acids interact strongly with bifunctional substrates such as sugars, diols, and a-hydroxycarboxylates in aqueous media. A few boronic acid-based receptors show enantioselectivities. For example, fluorescent sugar sensor (8) differentiates D- from L monosaccharides. Compounds 9 and (+)-10 were developed to diastereomerically derivative chiral diols, such that their ees could be determined by proton ($^1$H) NMR. Exemplary embodiments of enantioselective indicator-displacement assays may be based on the reversible covalent interactions in aqueous media between aromatic boronic acids and α-hydrocarboxylates or vicinal diols. More specifically, an enantioselective indicator-displacement assay based on a chiral boronic acid receptor and a colorimetric indicator pyrocatechol violet (PV) may be used to determine the ees of α-hydroxycarboxylate samples. The concentration of a sample, which is needed for its ee determination, may be measured with an achiral displacement assay prior to the ee analysis. Examples 8-12 demonstrate a two-measurement protocol (Scheme 1), in which the ee values of three phenyllactic acid (PL) samples were determined with 15-20% error. In addition, according to the present invention, the sensitivity of the assay can be tuned by changing the indicators and other substrates can be analyzed with this assay. Thus, the present invention provides experimental protocols that improve the accuracy of ee determination.

Figure 21A:
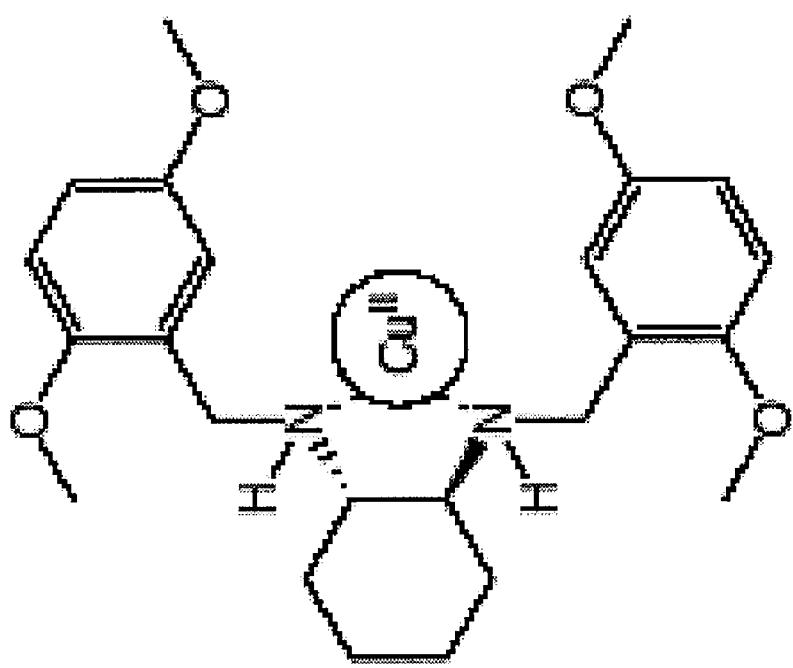
FIG. 21A illustrates the structure of (S,S)-22-$Cu^{II}$/L-amino acid ternary complex.
Figure 21B:
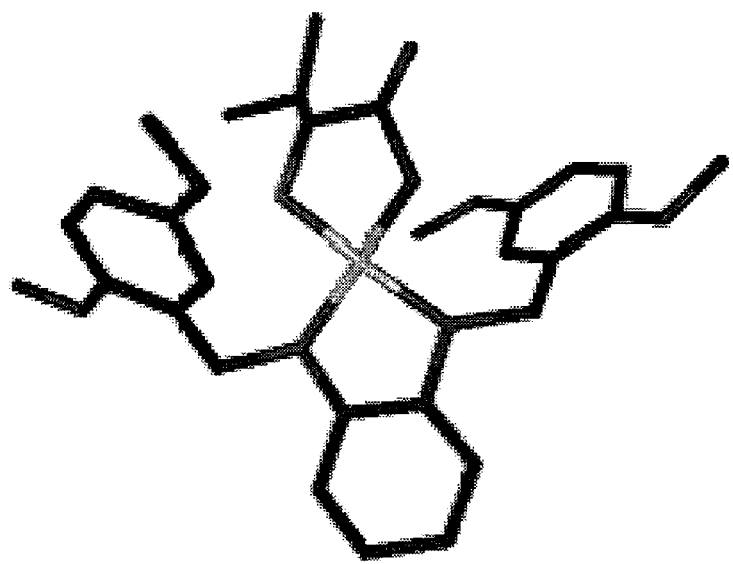
FIG. 21B illustrates structural hypothesis to explain the observed stereoselectivity. Steric interactions between the dimethoxybenzyl groups and the amino acid R group destabilize the (S,S)-22-$Cu^{II}$/L-amino acid ternary complex.
Figure 21B:
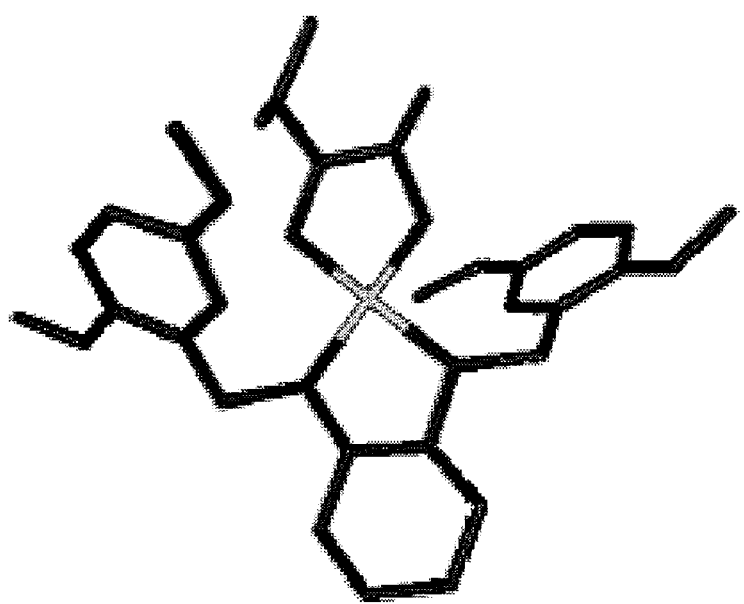
Figure 21C:
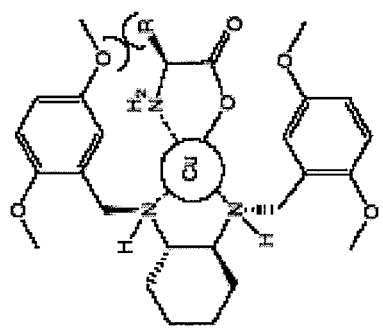
FIG. 21C illustrates structural hypothesis to explain the observed stereoselectivity. Steric interactions between the dimethoxybenzyl groups and the amino acid R group destabilize the (S,S)-22-$Cu^{II}$/L-amino acid ternary complex.
Figure 21C:
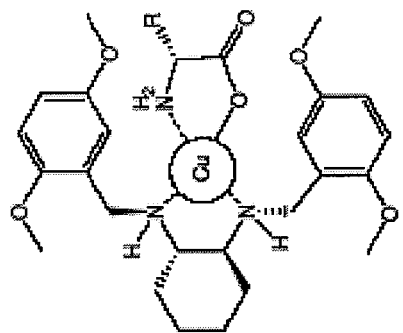
Figure 22:
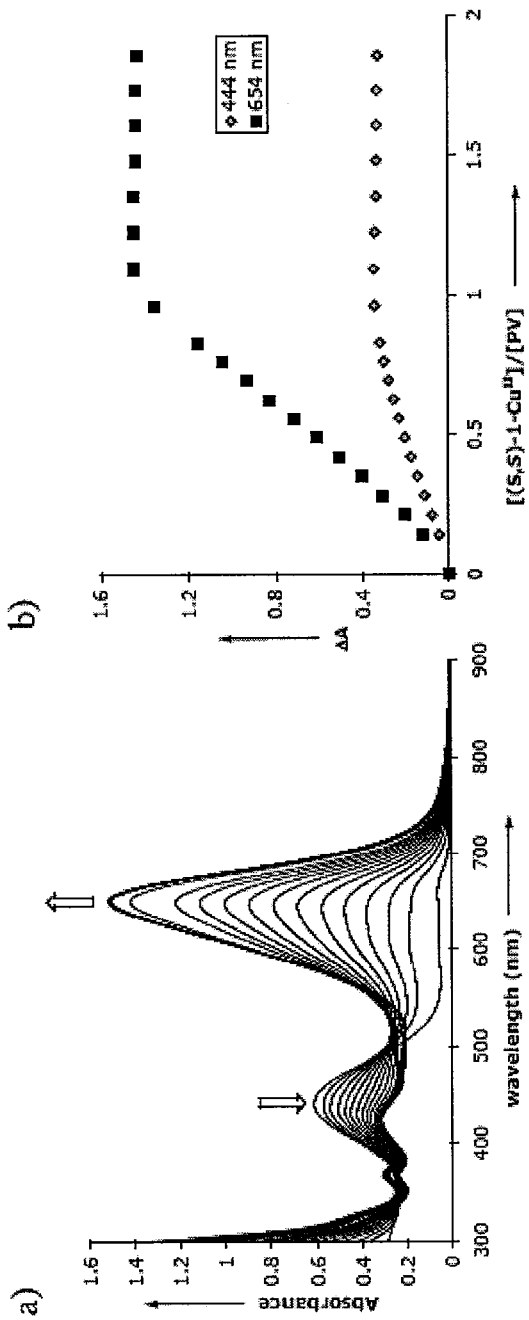
FIG. 22A illustrates UV-vis spectral modulations for the addition of (S,S)-22-$Cu^{II}$ to a solution of PV (44 ∝M) in a 1:1 MeOH:H$_2$O 50 mM HEPES buffer, pH=7.0.
FIG. 22B illustrates association isotherms at 444 nm and 654 nm for the addition of (S,S)-22-$Cu^{II}$ to a solution of PV (44 μM) in a 1:1 MeOH:H$_2$O 50 mM HEPES buffer, pH=7.0.
Figure 23:
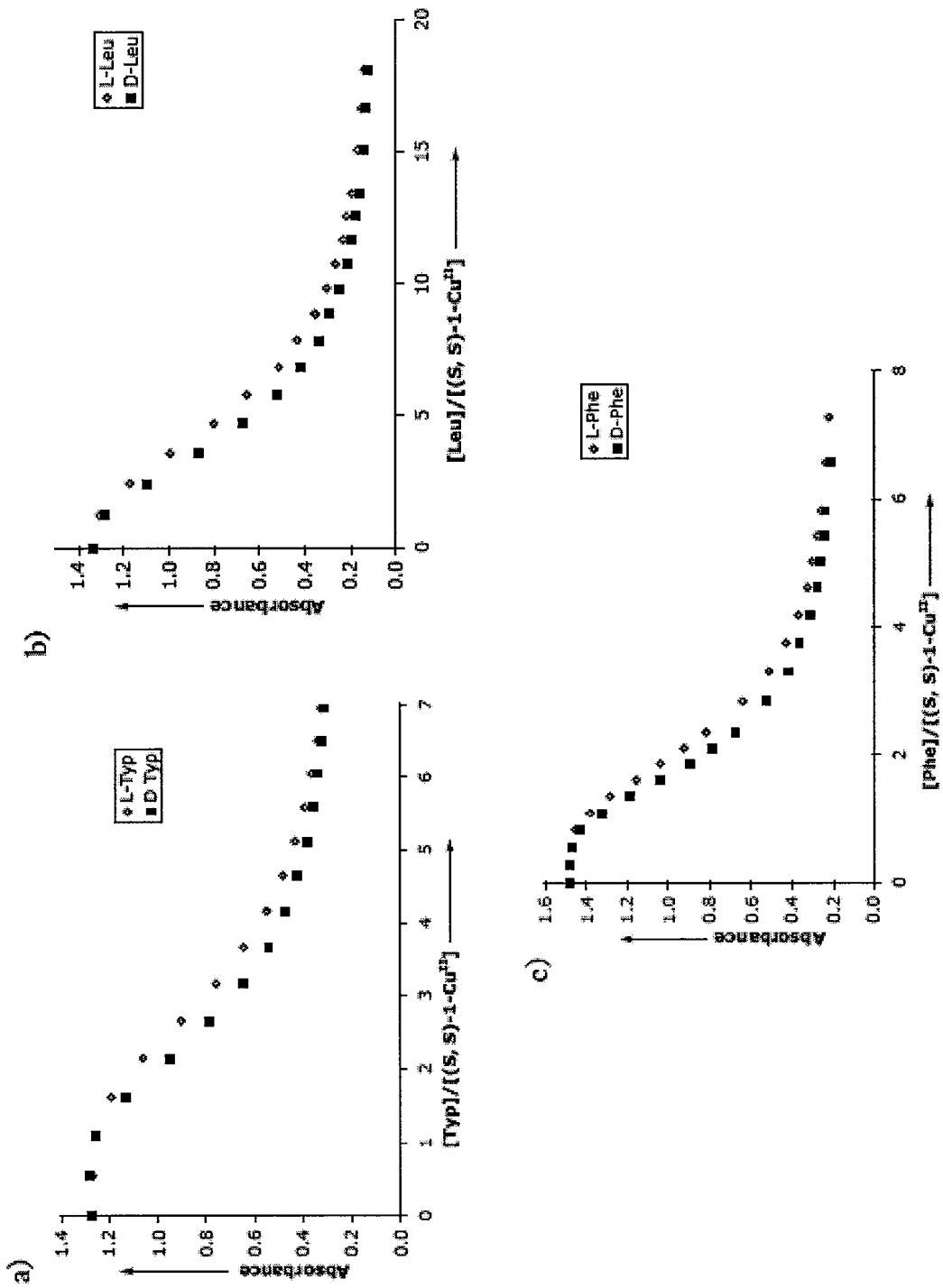
FIG. 23A illustrates a displacement isotherm at 653 nm for the addition of D and L tryptophan into a solution of PV (44 μM) and (S,S)-22-$Cu^{II}$ (380 μM). Displacement titrations performed in 1:1 MeOH:H$_2$O 50 mM HEPES buffer, pH=7.0.
FIG. 23B illustrates a displacement isotherm at 653 nm for the addition of D and L leucine to a solution of PV (44 μM), (S,S)-22-$Cu^{II}$ (380 μM).
FIG. 23C illustrates a displacement isotherm at 653 nm for the addition of D and L phenylalanine to a solution of PV (44 μM), (S,S)-22-$Cu^{II}$ (383 μM).
Figure 24:
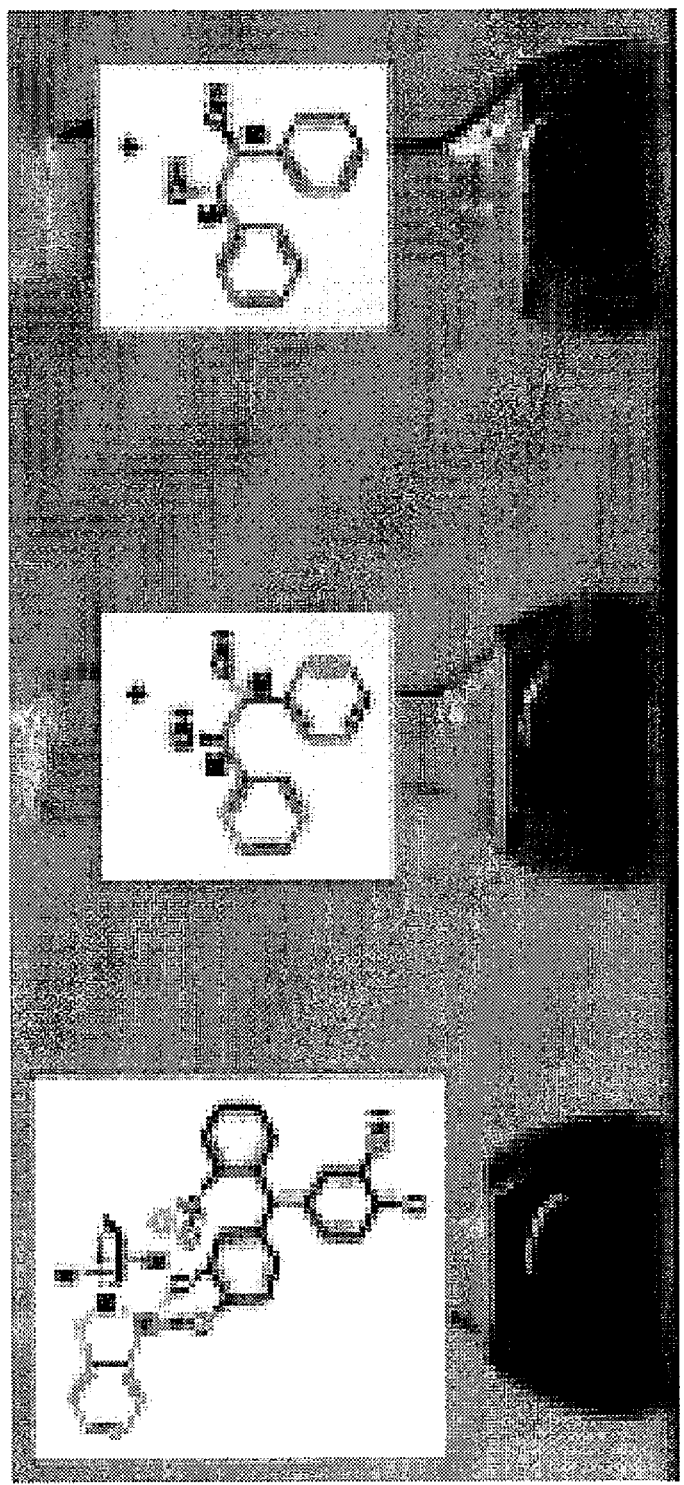
FIG. 24 illustrates the visible color of indicator-displacement assays according to the teaching of the present invention.

Due to their biological significance, α-amino acids have been widely studied from the perspective of enantioselective recognition. Despite this, there exist very few ee sensors for free amino acids. According to some non-limiting embodiments of the present invention, Indicator Displacement Analyses (IDA) may be directed to amino acid detection by using metal coordination as the primary associative interaction. This approach takes advantage of the large absorbance shifts afforded when indicators such as pyrocatechol violet (PV) coordinate metal ions, as well as the structural organization of cyclic α-amino acid-metal ion chelates. The coordinatively unsaturated trans-diaminocyclohexane (DACH) derived $Cu^{II}$ complex (S,S)-22-$Cu^{II}$ (FIG. 21A) was designed as a host complex. This species is envisioned to be capable of associating with both the indicator PV and amino acid guests in a bidentate fashion. Further, (S,S)-22-$Cu^{II}$ presents the $Cu^{II}$ center in a chiral $C_2$ symmetric environment to selectively accommodate one amino acid enantiomer. The ligand (S,S)-22 is prepared from commercially available materials via a one-step reductive amination procedure (see Example 13).

Control of the multiple coordinative equilibria involved in the IDA necessitates consideration of the relative abilities of the species involved to act as ligands for $Cu^{II}$. Enantioselectivity is expected to arise from diastereomeric interactions within a host/guest complex. In light of the ability of α-amino acids to form stable 2:1 complexes with $Cu^{II}$, it is desirable that (S,S)-22-$Cu^{II}$ be robust enough to retain the $Cu^{II}$ center in the presence of several equivalents of amino acid. The formation constant (logK(M$^{-1}$)) for DACH:$Cu^{II}$ has been reported as 10.9 in aqueous solution, which is two orders of magnitude greater than the formation constants of $Cu^{II}$ complexes of hydrophobic amino acids under similar conditions. Although the formation constant of 22-$Cu^{II}$ is likely lower than that of DACH:$Cu^{II}$ because the vicinal amines are secondary, ternary amino acid complexes of 22-$Cu^{II}$ are expected to be relevant when the guest is not in great excess. Coincidentally, the formation constant of $Cu^{II}$:PV has been reported as 10.9, implying that the indicator has an affinity for $Cu^{II}$ comparable to that of 22 and of amino acid guests.

Titration of (S,S)-22-$Cu^{II}$ into a buffered 1:1 MeOH:H$_2$O solution of PV resulted in an increase in absorbance at 653 nm accompanied by a decrease in absorbance at 445 nm, giving the vivid color change from pale yellow to intense blue that is characteristic of PV coordination to a metal ion. The host/ indicator association isotherm exhibits sharp saturation near 1 equivalent of (S,S)-22-Cu$^{II}$, suggesting the formation of a stable (S,S)-1-Cu$^{II}$:PV complex (see Example 13).

Addition of α-amino acids to a solution of (S,S)-22-Cu$^{II}$ and PV resulted in displacement of PV from the Cu$^{II}$ center, giving a shift from the blue color of Cu$^{II}$-bound PV to the yellow of free PV. Of the five amino acids assayed (alanine (Ala), valine (Val), leucine (Leu), tryptophan (Typ) and phenylalanine (Phe)), all but Ala produced an enantioselective response, with the D-enantiomer displacing PV most effectively. It was found that the enantioselective response was contingent upon the host:indicator ratio and that roughly a seven-fold excess of (S,S)-22-Cu$^{II}$ over PV was optimal. Under the same conditions, the enantiomer of the host complex, (R,R)-22-Cu$^{II}$ was found to prefer L-amino acids to a similar degree that (S,S)-22-Cu$^{II}$ favors D-amino acids. The enantiomeric discrimination is nearly identical for Val, Leu, Typ and Phe, but the aromatic side chain containing amino acids displaced PV more effectively than those containing aliphatic side chains, which could result from an attractive π-π interaction in a ternary complex. Representative spectral modulations and displacement isotherm at 653 nm for Val are shown in FIGS. 19A and 19B respectively.

The displacement isotherms do not conform to the theoretical indicator displacement model, indicating that a more complex process is operative. Given the large affinity of α-amino acids for Cu$^{II}$, it is likely that (S,S)-1, as well as PV, is displaced toward the end of the titration when the amino acid is in large excess. While this deviation from standard IDA model behavior prohibits the estimation of host-guest formation constants, the enantioselective response of the sensing ensemble can successfully be used for ee determination.

Relationships between amino acid ee and absorbance were obtained at constant amino acid concentration under conditions that accentuated absorbance differences between enantiomers. The absorbance was monitored at 645 nm, so that the weaker binding L-enantiomer produced a larger absorbance. To optimize the sensitivity of the assay, the amino acid concentration that gave the greatest absorbance difference between the enantiomers was identified from the enantiomeric displacement isotherms (FIG. 19B). At that point, the concentrations of all species were increased (keeping relative concentrations constant) thus increasing the absorbance values produced by both enantiomers. By enhancing both signals in this way, the difference between the absorbance values caused by each enantiomer is amplified, thus augmenting the sensitivity.

Figure 19:
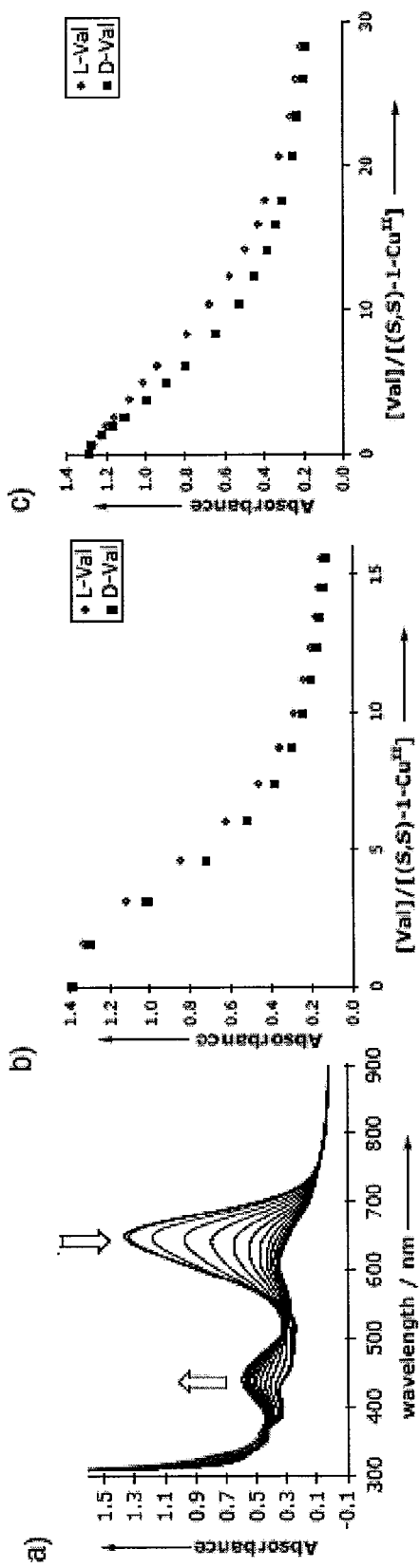
FIG. 19A illustrates UV-vis spectral modulations for the addition of D and L valine into a solution of PV (44 μM) and (S,S)-22-$Cu^{II}$ (332 μM).
FIG. 19B illustrates a displacement isotherm at 653 nm for the addition of D and L valine into a solution of PV (44 μM) and (S,S)-22-$Cu^{II}$ (332 μM).
FIG. 19C illustrates a displacement isotherm at 653 nm for the addition of D and L valine to a solution of PV (42 μM), Cu(OTf)$_2$ (341 μM) and (S,S)-22 (2.45 mM). Titrations performed in 1:1 MeOH:H$_2$O 50 mM HEPES buffer, pH=7.0.

In FIG. 19B, the greatest difference between the D and L isotherms is achieved at about 4.6 eq Val (relative to (S,S)-22-Cu$^{II}$), where the total absorbance values are still quite large and the signals cannot be increased significantly within the upper limit of the validity of Beer's Law (the absorbance caused by L-Val is 0.85). It was found that by increasing the concentration of (S,S)-22 in the ensemble, the greatest enantioselectivity is observed later in the titration (FIG. 19C), which is likely due to a more competitive displacement process. In FIG. 19C, significant enantioselectivity is observed at 12 eq Val, where L-Val elicits an absorbance response of 0.58. The concentrations of all species were multiplied from this point by a factor of 1.7 (1/0.58) to generate an ee curve with an absorbance maximum (at 100% L-Val) near 1.0. By adjusting the concentrations of the ensemble in this manner, the absorbance difference between enantiomers was roughly doubled relative to the initial conditions.

Figure 20:
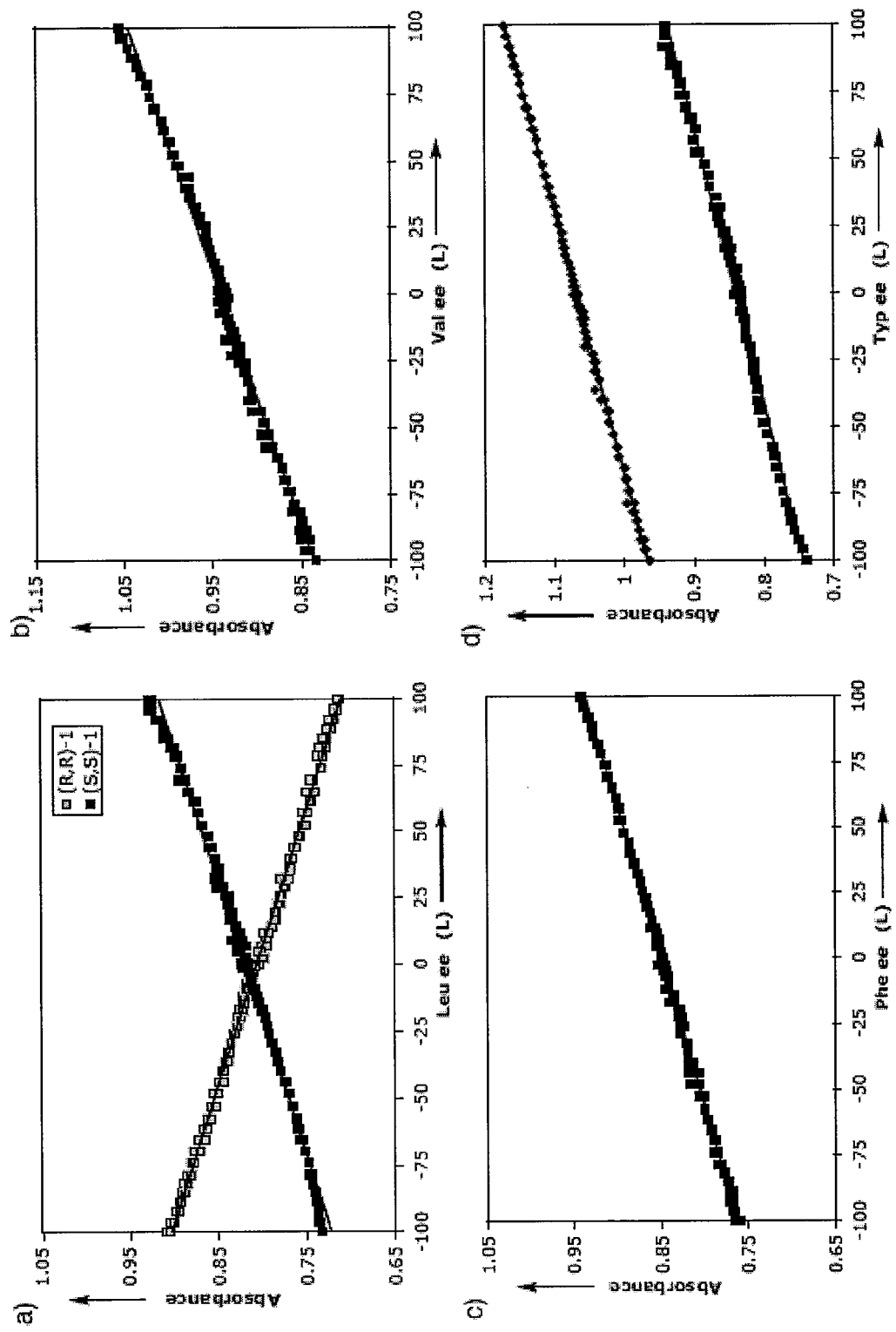
FIG. 20A illustrates the absorbance at 645 nm as a function of ee for Leu (6.6 mM) in a solution of PV (75 μM), Cu(OTf)$_2$ (590 μM) and 1 (both enantiomers) (4.2 mM). All ee curves were obtained in 1:1 MeOH:H$_2$O 50 mM HEPES buffer, pH=7.0.
FIG. 20B illustrates the absorbance at 645 nm as a function of ee for Val (7.1 mM) in a solution of PV (75 μM), Cu(OTf)$_2$ (590 μM) and (S,S)-22 (4.2 mM).
FIG. 20C illustrates the absorbance at 645 nm as a function of ee for Phe (3.0 mM) in a solution of PV (72 μM), Cu(OTf)$_2$ (590 μM) and (S,S)-22 (4.2 mM).
FIG. 20D illustrates the absorbance at 645 nm as a function of ee for Typ (4.5 mM squares, 3.0 mM diamonds) in a solution of PV (90 μM), Cu(OTf)$_2$ (775 μM) and (S,S)-22 (5.9 mM).

The ee curves presented in FIG. 20 are remarkably linear ($R_2$>0.99), and in all cases span an absorbance range greater than 0.2 absorbance units, demonstrating the ensemble to be useful over the entire ee range. FIG. 20A shows that ee curves for Leu generated with (S,S)-22-Cu$^{II}$ and (R,R)-22-Cu$^{II}$ at identical concentrations exhibit a mirror image relationship, as required by the principles of stereochemistry. Decreasing the total concentration of amino acid at which the ee curve is generated gives a larger overall absorbance at 645 nm, as shown for Typ (FIG. 20D). At a lower amino acid concentration, the amino acid competes with PV for (S,S)-22-Cu$^{II}$ less effectively, and so a higher fraction of the indicator is bound to the host, giving a larger absorbance. The calibration curves were used to analyze the ees of various amino acid samples. By UVvis measurement samples of unknown ee were determined with an average error of 12%, as reported in Table 4.

TABLE 4

Enantiomeric excess determinations of amino acid samples by UV-vis method.

| Amino Acid Sample | ee (Actual) | ee (Determined) |
|---|---|---|
| valine | | |
| A | −50% | −54% |
| B | 25% | 12% |
| C | −65% | −88% |
| phenylalanine | | |
| D | 67% | 81% |
| E | −82% | −78% |
| F | 50% | 57% |
| tryptophan | | |
| G | 90% | 92% |
| H | 33% | 58% |
| I | −71% | −56% |

The enantioselectivity of this IDA arises from in a mixed ligand Cu$^{II}$ complex involving 22 and the amino acid guest. The preference for D-amino acids exhibited by (S,S)-22-Cu$^{II}$ is rationalized by the following analysis. The dimethoxybenzyl groups of 22-Cu$^{II}$ are expected to orient as shown in FIG. 21 to avoid A$^{1,2}$-strain with the cyclohexane ring, creating a $C_2$ symmetric cavity in which the Cu$^{II}$ resides. Assuming a square planer Cu$^{II}$ geometry, chelation of a D-amino acid allows the R group to avoid steric interactions with the dimethoxybenzyl groups that the bound L-enantiomer cannot evade. This structural arrangement is expected to stabilize the D-complex over the L-complex, and give rise to the more effective indicator displacement observed with (S,S)-22-Cu$^{II}$ for D-amino acids.

Thus, the present invention provides an enantioselective IDA for amino acids. The sensing ensemble allows for the measurement of non-derivatized amino acid ees by a simple technique (UV-vis spectrophotometry) and requires trivial synthesis. More broadly, the methods and compositions of the present invention provides enantioselective IDAs that may be useful for rapid and simple means of ee determination for a variety of substrates.

EXAMPLES

The following examples are included to demonstrate specific embodiments of the invention. It should be appreciated by those of skill in the art that the techniques disclosed in the examples that follow represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention.

Example 1

General Methods $^1$H and $^{13}$C NMR spectra were recorded on a Varian Unity Plus 300 spectrometer. UV-vis measurements were performed on a Beckman DU-70 UV-vis spectrometer. Low-resolution and high-resolution mass spectra were measured with Finnigan TSQ70 and VG Analytical ZAB2-E instruments, respectively. Reagents were used as purchased from various commercial sources.

Example 2

General Procedures for Syntheses of Boronic Receptors (Compounds 1-3)

A). 2-Formylbenzeneboronic acid (1 mmol) was dissolved in anhydrous CH$_3$OH (2.5 mL) under argon protection. Substituted pyrrolidine (1 mmol) was added dropwise to the solution which was stirred for 16 hr before NaBH$_4$ (0.75 mmol) was added slowly. The solution was stirred at r.t. for 1 hr, followed by addition of another batch NaBH$_4$ (0.75 mmol). One hr later, the solvent was removed under vacuum and the residue was diluted with CH$_2$Cl$_2$ (25 mL). The white precipitate was removed with vacuum filtration, with the filtrate subsequently concentrated. The residue was either chromatographed on neutral alumina column (0-4% CH$_3$OH in CH$_2$Cl$_2$), or precipitated from a CH$_2$Cl$_2$ solution through addition of hexanes to yield the pure product.

B). 2-Formylbenzeneboronic acid (1.57 mmol) was dissolved in anhydrous dichloroethane (6.3 mL) under argon protection. After the slow addition of (R,R)- or (S,S)-2,5-bis(methoxymethyl)-pyrrolidine (1.57 mmol), the solution was stirred at r.t. for 16 hr. AcOH (1.57 mmol) was added followed by NaBH(OAc)$_3$ (2.36 mmol) and the solution was stirred for a further 6 hr. Solvent was removed under vacuum and the residue was diluted with CH$_2$Cl$_2$ (25 mL) before the precipitate was removed with vacuum filtration. The filtrate was concentrated and the residue was subjected to neutral alumina chromatography (0-2% CH$_3$OH in CH$_2$Cl$_2$) to afford the pure product.

Compound 1. $^1$H NMR (300 MHz, CD$_3$OD) δ 7.57 (d, J=6.7 Hz, 1H), 7.20 (m, 3H), 4.13 (s, 2H), 3.10 (m, 4H), 2.06 (m, 4H); HRMS (CI): calcd. (M+H)$^+$ 206.1352, (3M-3H$_2$O+H)$^+$ 562.3584. Found 206.1347, 562.3606. MS (CI): calcd. (3M-3H$_2$O+H)$^+$ 562.3. Found 562.0.

Compound (S,S)-2. $^1$H NMR (300 MHz, CDCl$_3$+1 drop CD$_3$OD) δ 7.83 (m, 1H), 7.25 (m, 3H), 4.10 (d, J=13.1 Hz, 1H), 3.87 (d, J=12.8 Hz, 1H), 3.31 (d, J=5.1 Hz, 4H), 3.23 (s, 6H), 3.19 (m, 2H), 2.02 (m, 2H), 1.70 (m, 2H); $^{13}$C NMR (75.5 MHz, CDCl$_3$+1 drop CD$_3$OD) δ 142.5, 136.3, 130.3, 130.1, 127.3, 73.8, 61.2, 59.1, 56.4, 27.2; HRMS (CI) calcd. (M+H)$^+$ 294.1877. Found 294.1875. MS (CI): calcd (M+H)$^+$ 294.2, (3M-3H$_2$O+H)$^+$ 862.6. Found 294.0, 827.0.

Compound (R,R)-2. $^1$H NMR (300 MHz, CDCl$_3$+1 drop CD$_3$OD) δ 7.84 (m, 1H), 7.29 (m, 2H), 7.23 (m, 1H), 4.11 (d, J=12.8 Hz, 1H), 3.88 (d, J=13.1 Hz, 1H), 3.33 (d, J=5.1 Hz, 4H), 3.24 (s, 6H), 3.20 (m, 2H), 2.03 (m, 2H), 1.72 (m, 2H); HRMS (CI): calcd. (M+H)$^+$ 294.1877. Found 294.1884. MS (CI): calcd (M+H)$^+$ 294.2, (3M-3H$_2$O+H)$^+$ 862.6. Found 294.0, 826.7.

(S)-3. $^1$H NMR (300 MHz, CDCl$_3$+1 drop CD$_3$OD) δ 7.84 (m, 1H), 7.29 (m, 2H), 7.17 (m, 1H), 4.18 (d, J=12.3 Hz, 1H), 3.48 (d, J=12.3 Hz, 1H), 3.40 (dd, J=5.6, 9.5 Hz, 1H), 3.29 (dd, J=5.6, 9.7 Hz, 1H), 3.28 (s, 3H), 2.81 (m, 2H), 2.29 (m, 1H), 2.01 (m, 1H), 1.73 (m, 3H); $^{13}$C NMR (75.5 MHz, CDCl$_3$+1 drop CD$_3$OD) δ 142.6, 136.1, 130.12, 130.07, 127.4, 75.2, 63.7, 62.2, 59.1, 54.1, 28.6, 22.8; HRMS (CI): calcd. (M−OH)$^+$ 232.1509, (3M−3H$_2$O+H)$^+$ 694.4370. Found 232.1517, 694.4404.

Example 3

Derivation of Eq. 3

Beer's Law and Indicator Mass Balance:

$$A = \epsilon_I b[I] + \epsilon_{HI} b[HI] \quad (1)$$

$$[I] + [HI] = I_t \quad (2)$$

Solution Equilibria:

$$\frac{[HG_R]}{[G_R][H]} = K_R \quad (3)$$

$$\frac{[HG_S]}{[G_S][H]} = K_S \quad (4)$$

$$\frac{[HI]}{[I][H]} = K_I \quad (5)$$

Host & Guest Mass Balances:

$$[G_R] + [G_S] + [HG_R] + [HG_S] = G_t \quad (6)$$

$$[H] + [HI] + [HG_R] + [HG_S] = H_t \quad (7)$$

ee Expression:

$$ee_R = \frac{([G_R] + [HG_R]) - ([G_S] + [HG_S])}{G_t} \quad (8)$$

From (1) and (2)

$$[I] = \frac{\epsilon_{HI} b I_t - A}{b \Delta \epsilon} \quad (9)$$

$$[HI] = \frac{A - \epsilon_I b I_t}{b \Delta \epsilon} \quad (10)$$

$$\Delta \epsilon = \epsilon_{HI} - \epsilon_I$$

From (9), (10) and (5)

$$[H] = \frac{[HI]}{K_I[I]} = \frac{\epsilon_I b I_t - A}{K_I (A - \epsilon_{HI} b I_t)} \quad (11)$$

From (7) and (8)

Define $X \equiv [G_R] + [HG_R]$, $Y \equiv [G_S] + [HG_S]$ $$X + Y = G_t$$

Then $$X - Y = G_t ee_R$$

$$X = [G_R] + [HG_R] = \frac{G_t}{2}(1 + ee_R) \quad (12)$$

$$Y = [G_S] + [HG_S] = \frac{G_t}{2}(1 - ee_R) \quad (13)$$

$$[HG_R] = K_R[G_R][H] \quad (3)$$

$$[G_R] + [HG_R] = \frac{G_t}{2}(1 + ee_R) \quad (12)$$

(3) and (12) give:

$$[HG_R] = \frac{(1 + ee_R)G_t[H]K_R}{2(1 + [H]K_R)} \quad (14)$$

$$[G_R] = \frac{(1 + ee_R)G_t}{2(1 + [H]K_R)} \quad (15)$$

(11) and (14) give:

$$[HG_R] = \frac{K_R G_t (1 + ee_R)(\varepsilon_I b I_t - A)}{2[A(K_I - K_R) - b I_t(\varepsilon_{HI} K_I - \varepsilon_I K_R)]} \quad (16)$$

Likewise, $$[HG_S] = \frac{(1 - ee_R)G_t[H]K_S}{2(1 + [H]K_S)} = \frac{K_S G_t (1 - ee_R)(\varepsilon_I b I_t - A)}{2[A(K_I - K_S) - b I_t(\varepsilon_{HI} K_I - \varepsilon_I K_S)]} \quad (17)$$

From (7), (10), (11), (16) and (17):

$$[H] + [HI] + [HG_R] + [HG_S] = H_t \quad (7)$$

$$[HI] = \frac{A - \varepsilon_I b I_t}{b \Delta \varepsilon} \quad (10)$$

$$[H] = \frac{[HI]}{K_I[I]} = \frac{\varepsilon_I b I_t - A}{K_I(A - \varepsilon_{HI} b I_t)} \quad (11)$$

$$[HG_R] = \frac{K_R G_t (1 + ee_R)(\varepsilon_I b I_t - A)}{2[A(K_I - K_R) - b I_t(\varepsilon_{HI} K_I - \varepsilon_I K_R)]} \quad (16)$$

$$[HG_S] = \frac{K_S G_t (1 - ee_R)(\varepsilon_I b I_t - A)}{2[A(K_I - K_S) - b I_t(\varepsilon_{HI} K_I - \varepsilon_I K_S)]} \quad (17)$$

The A vs. ee relationship is:

$$\frac{A - \varepsilon_I b I_t}{b \Delta \varepsilon} + \frac{\varepsilon_I b I_t - A}{K_I(A - \varepsilon_{HI} b I_t)} + \frac{K_R G_t (1 + ee_R)(\varepsilon_I b I_t - A)}{2[A(K_I - K_R) - b I_t(\varepsilon_{HI} K_I - \varepsilon_I K_R)]} + \frac{K_S G_t (1 - ee_R)(\varepsilon_I b I_t - A)}{2[A(K_I - K_S) - b I_t(\varepsilon_{HI} K_I - \varepsilon_I K_S)]} = H_t$$

$\varepsilon_I$, $\varepsilon_{HI}$, $K_I$—From 1:1 Host/Indicator Isotherm
$K_R$, $K_S$—From Displacement Assay
$I_t$, $H_t$, $G_t$—Gravimetric

Example 4

Determination of Association Constants between Receptors and Indicators ($K_I$)

Figure 5A:
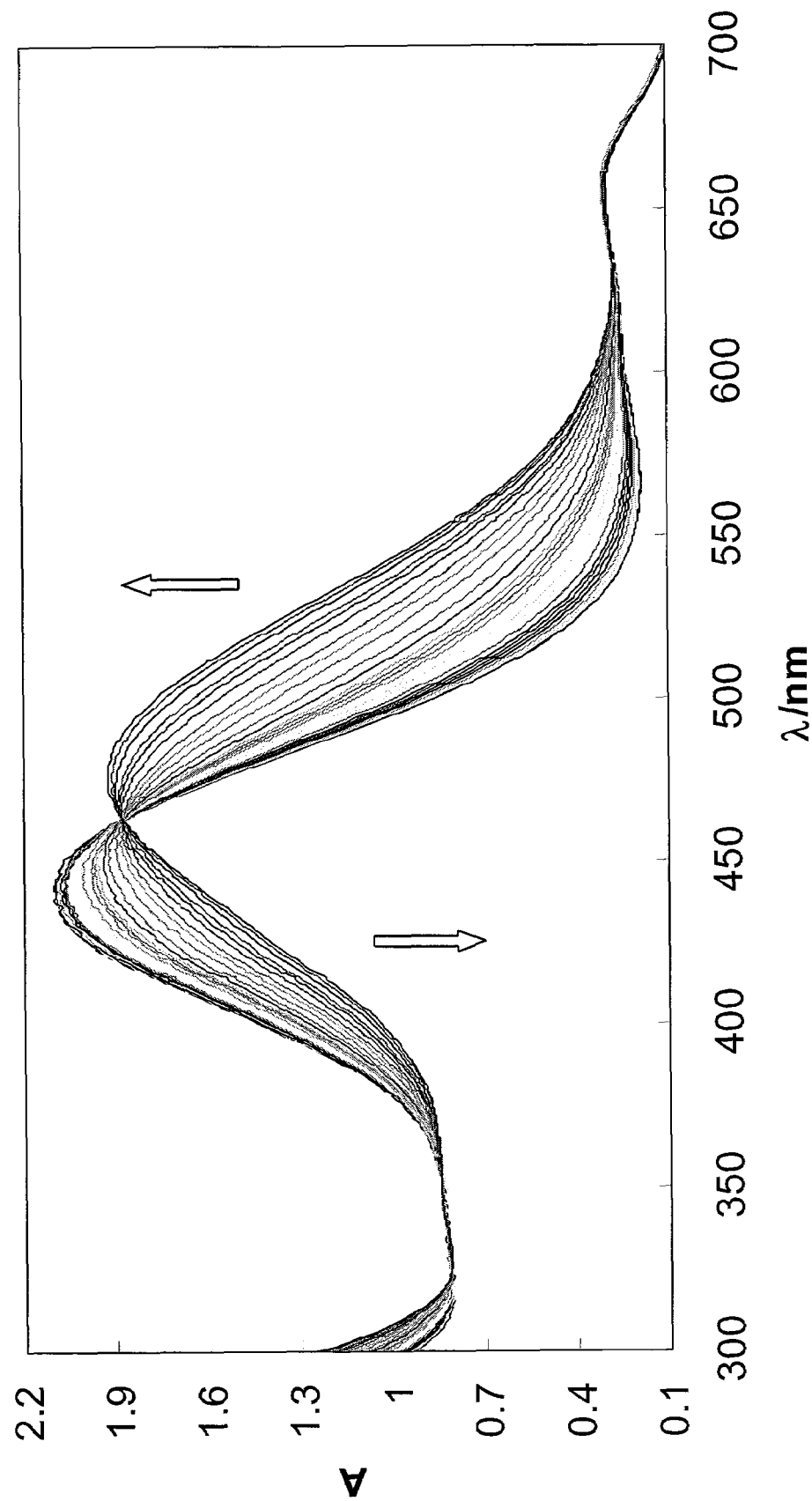
FIG. 5A presents absorbance spectra of PV (149 µM) in 75% methanolic aqueous solution buffered with 10 mM HEPES at pH 7.4 in the presence of 0-1.3 mM of Compound 1.
Figure 5B:
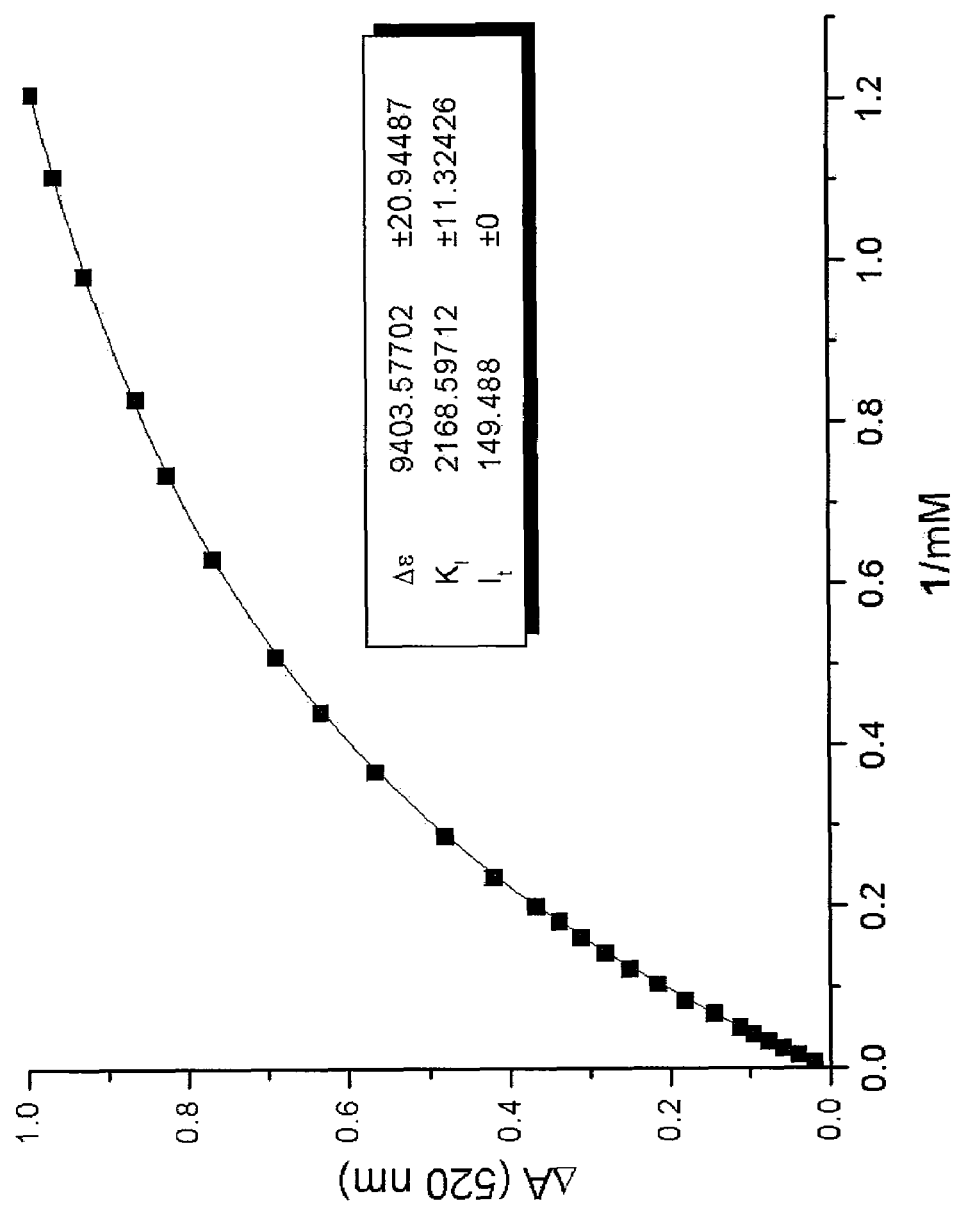
FIG. 5B presents graphically the curve fitting of absorbance change vs. receptor concentration at 520 nm (Origin® 5.0).

A solution of PV (149 μM) and Compound 1 (2.22 mM) was titrated into a UV cuvette containing a solution of PV (149 μM) at r.t. (FIG. 5A). The absorbance change (AA) was plotted against the increasing total concentration of Compound 1 at 520 nm (FIG. 5B). The association constant ($K_I$) was determined through least squares regression curve-fitting of the data at 520 nm with the 1:1 binding isotherm equation.

Example 5

Determination of Association Constants between Receptors and α-hydroxyacids ($K_R$, $K_S$)

Figure 6A:
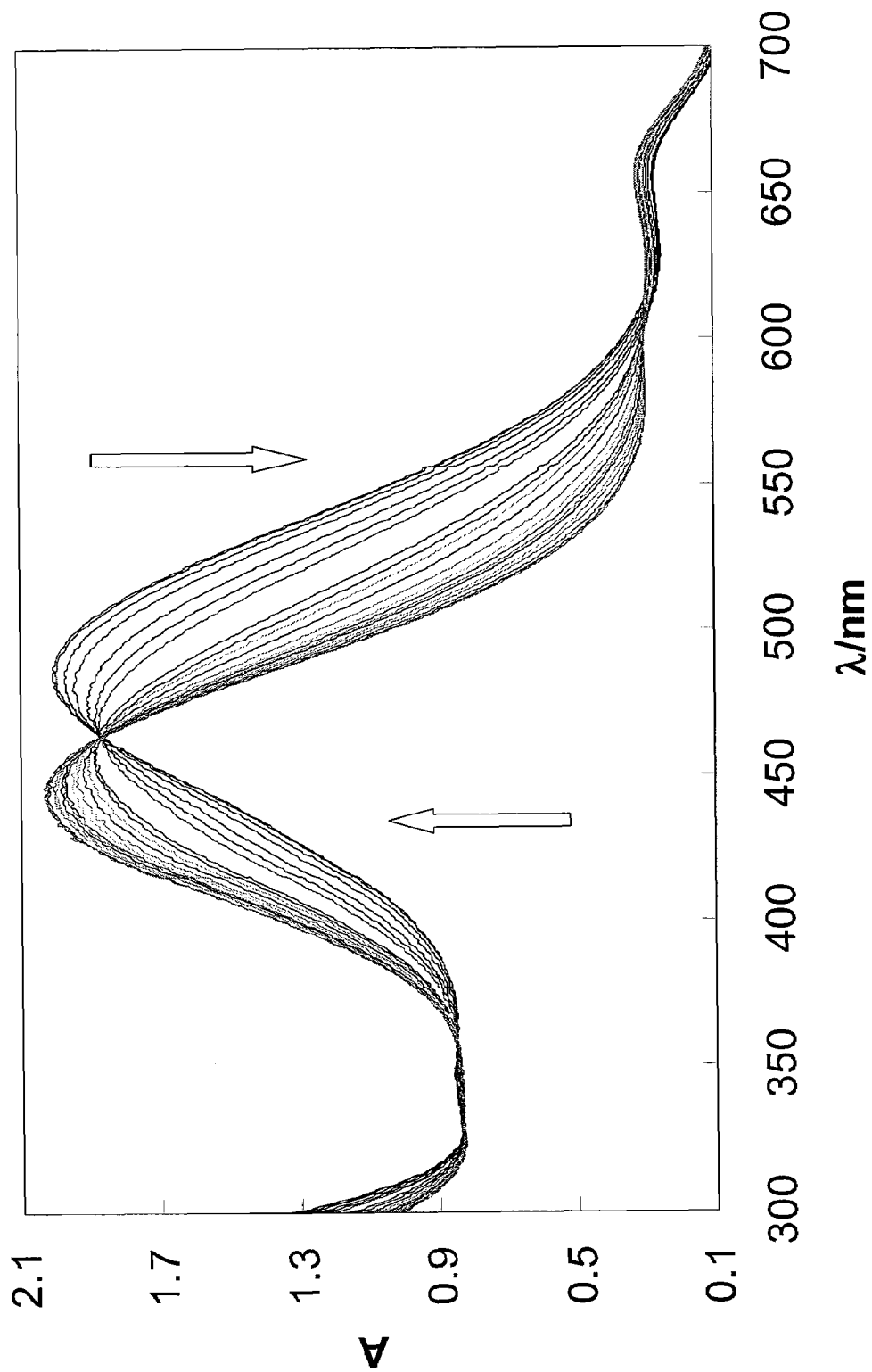
FIG. 6A presents absorbance spectra of PV (149 µM) and Compound (S,S)-2 (0.510 mM) in 75% methanolic aqueous solution buffered with 10 mM HEPES at pH 7.4 in the presence of 0-0.15 mM of D-PL.
Figure 6B:
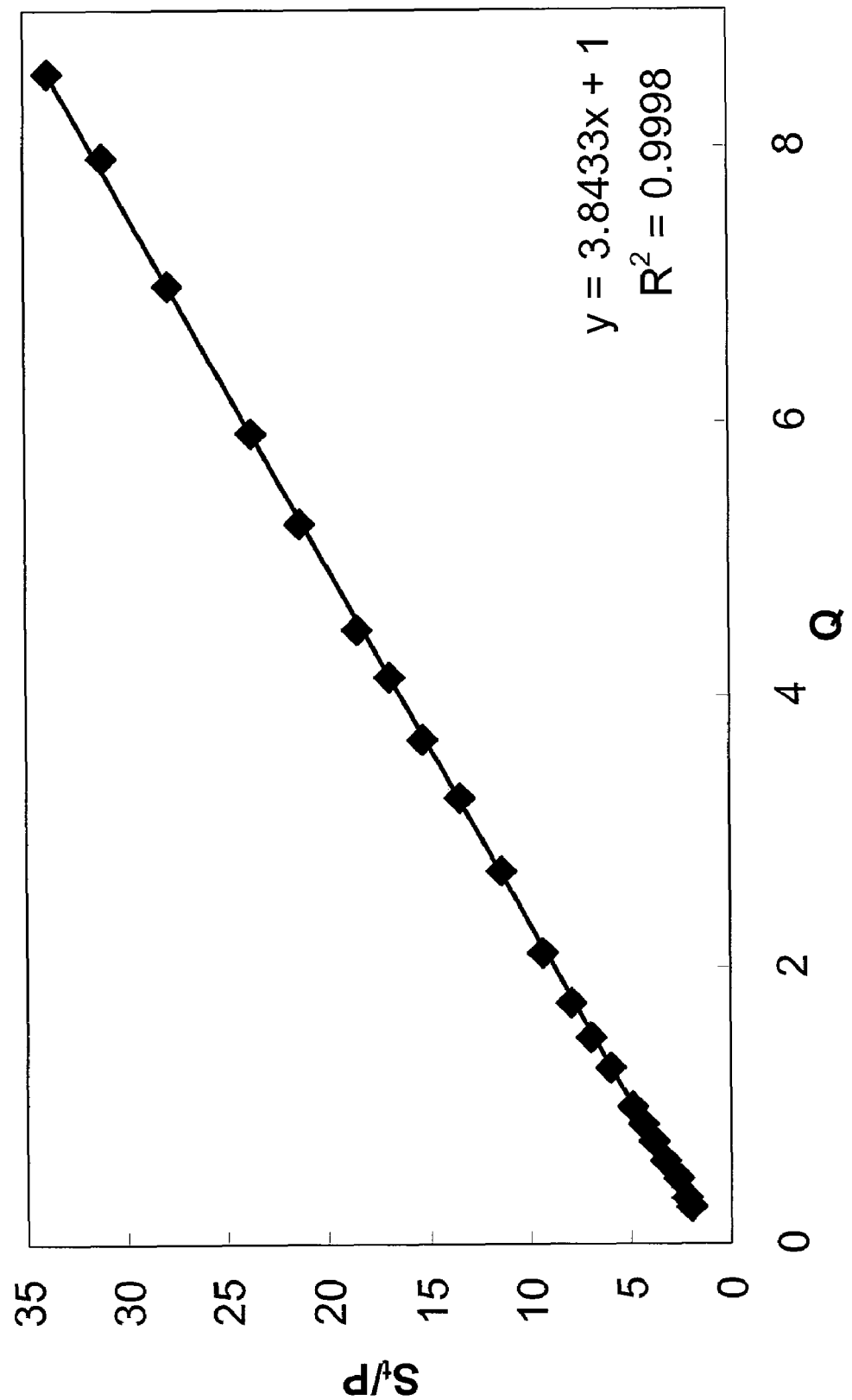
FIG. 6B presents graphically a $S_f/P$ vs. Q plot for competitive binding method with data at 520 nm.
Figure 7A:
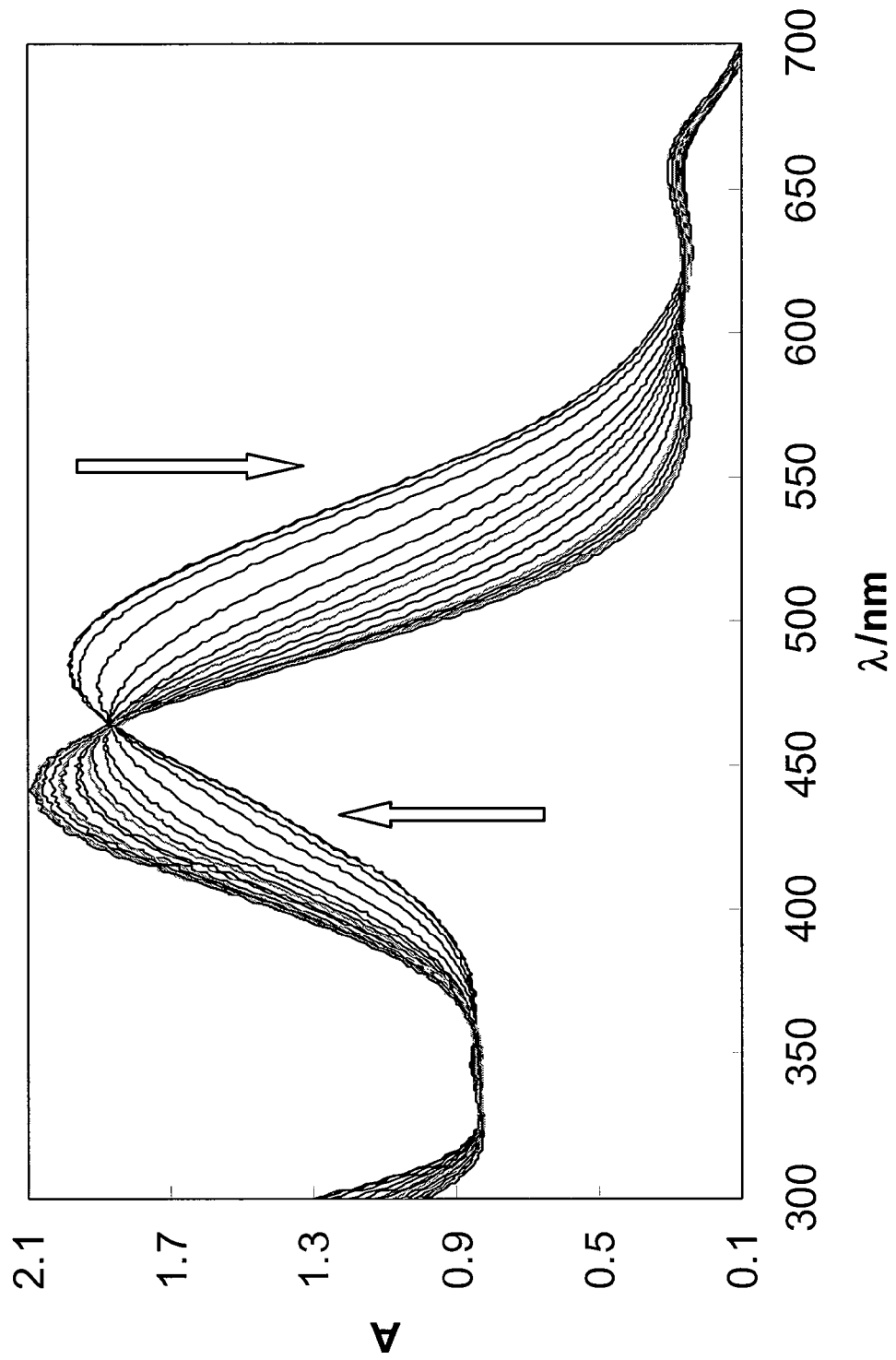
FIG. 7A presents absorbance spectra of PV (149 µM) and Compound (S,S)-2 (0.510 mM) in 75% methanolic aqueous solution buffered with 10 mM HEPES at pH 7.4 in the presence of 0-0.15 mM of L-PL.
Figure 7B:
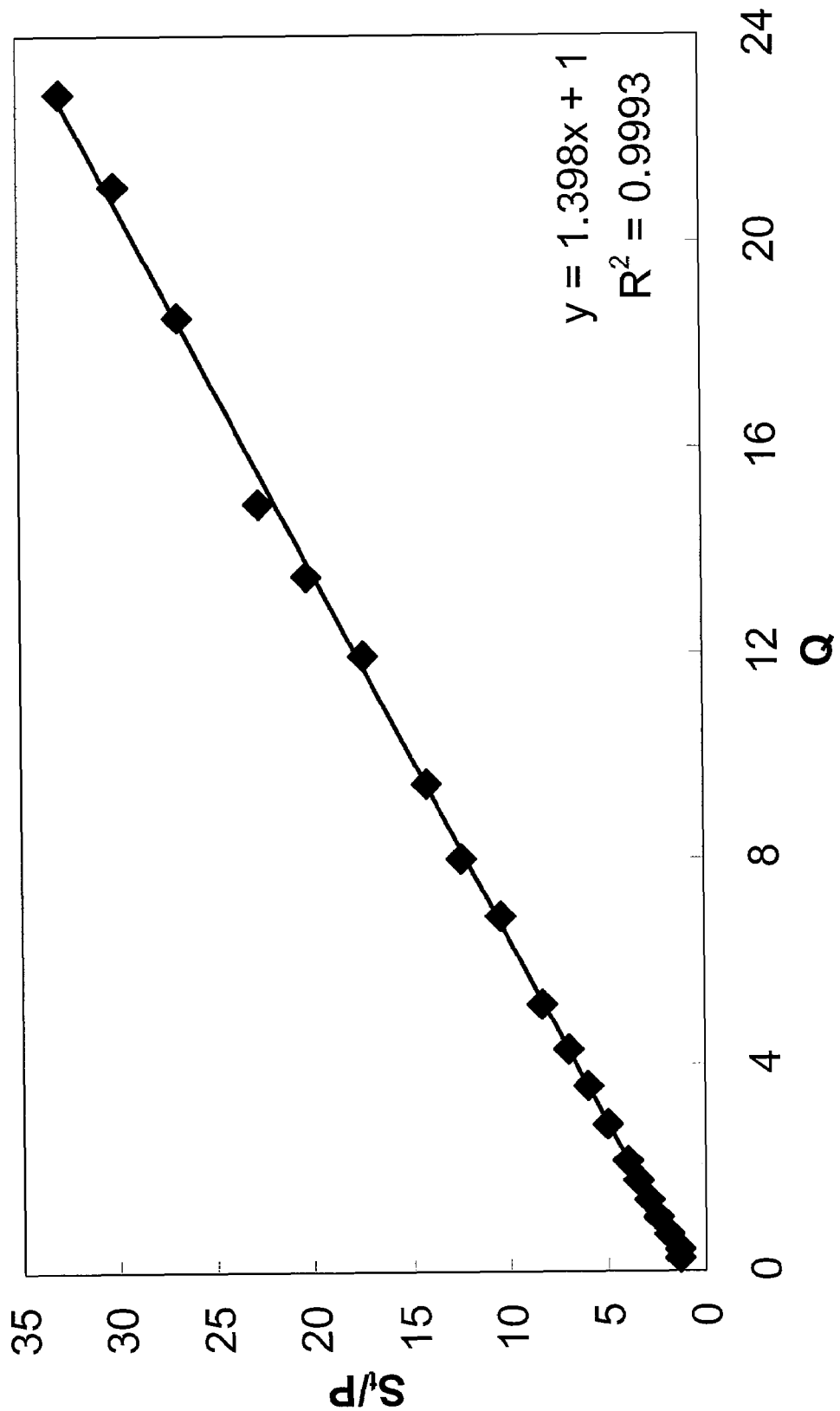
FIG. 7B graphically presents a $S_f/P$ vs. Q plot[2,3] for competitive binding method with data at 520 nm.

A solution of PV (149 μM), Compound (S,S)-2 (0.510 mM) and D-PL (30.0 mM) was titrated into a UV cuvette containing a solution of PV (149 μM) and Compound (S,S)-2 (0.51 mM) at r.t. The absorbance at 520 nm was recorded after at least 1 min to allow the system reaching equilibrium (FIG. 6A). The absorbance change (AA) was plotted against the ratio of D-PL concentration over Compound (S,S)-2 concentration (FIG. 3). The association constant ($K_R$) was determined with the competitive binding method with the data at 520 nm (FIG. 6B). (See also FIG. 7.)

Example 6

Determination of A-ee Correlation

Figure 8A:
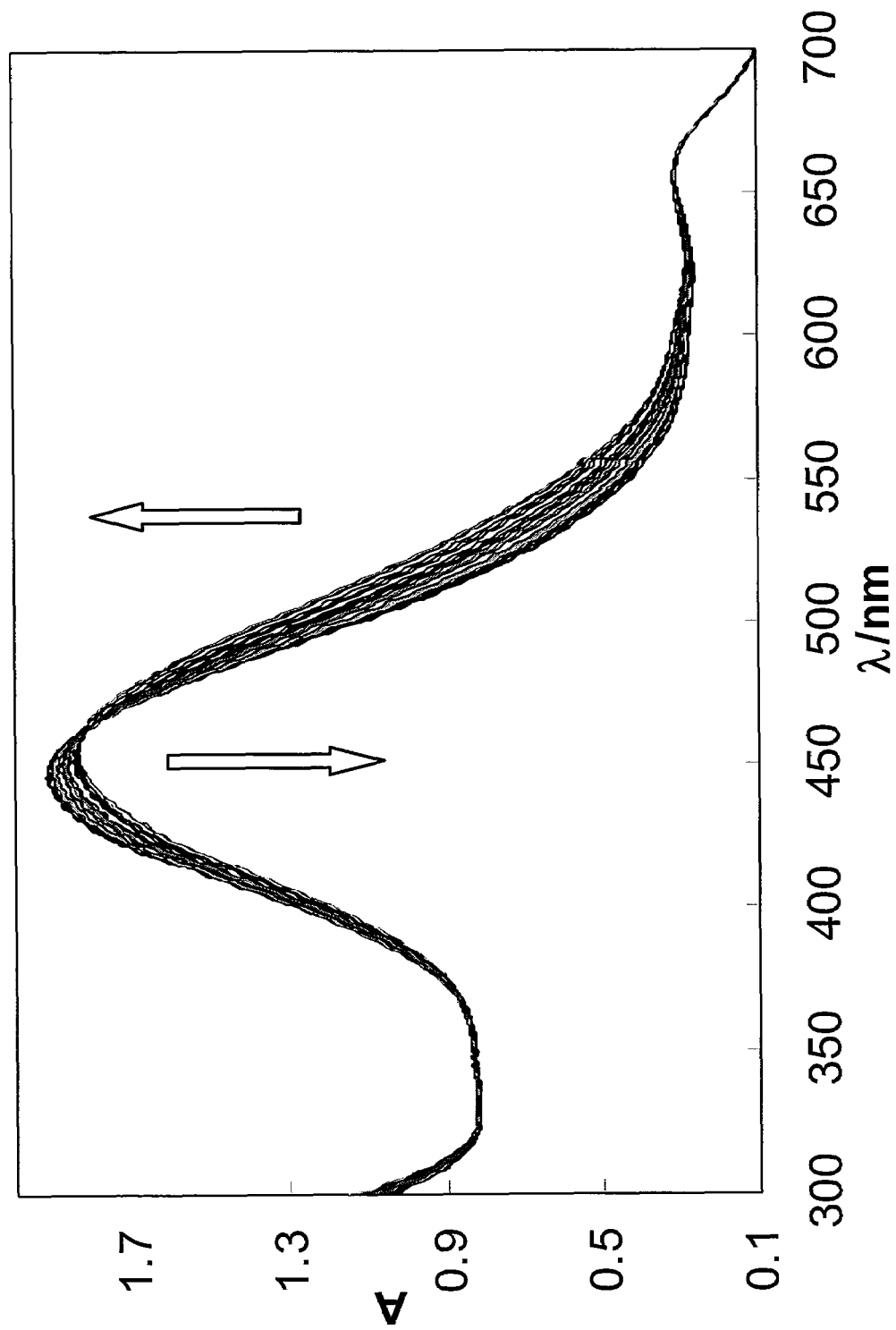
FIG. 8A presents absorbance spectra of PV (149 µM), Compound (S,S)-2 (0.510 mM) and PL (3.00 mM) in 75% methanolic aqueous solution buffered with 10 mM HEPES at pH 7.4 with the ee of D-PL changes from −1 to 1.
Figure 8B:
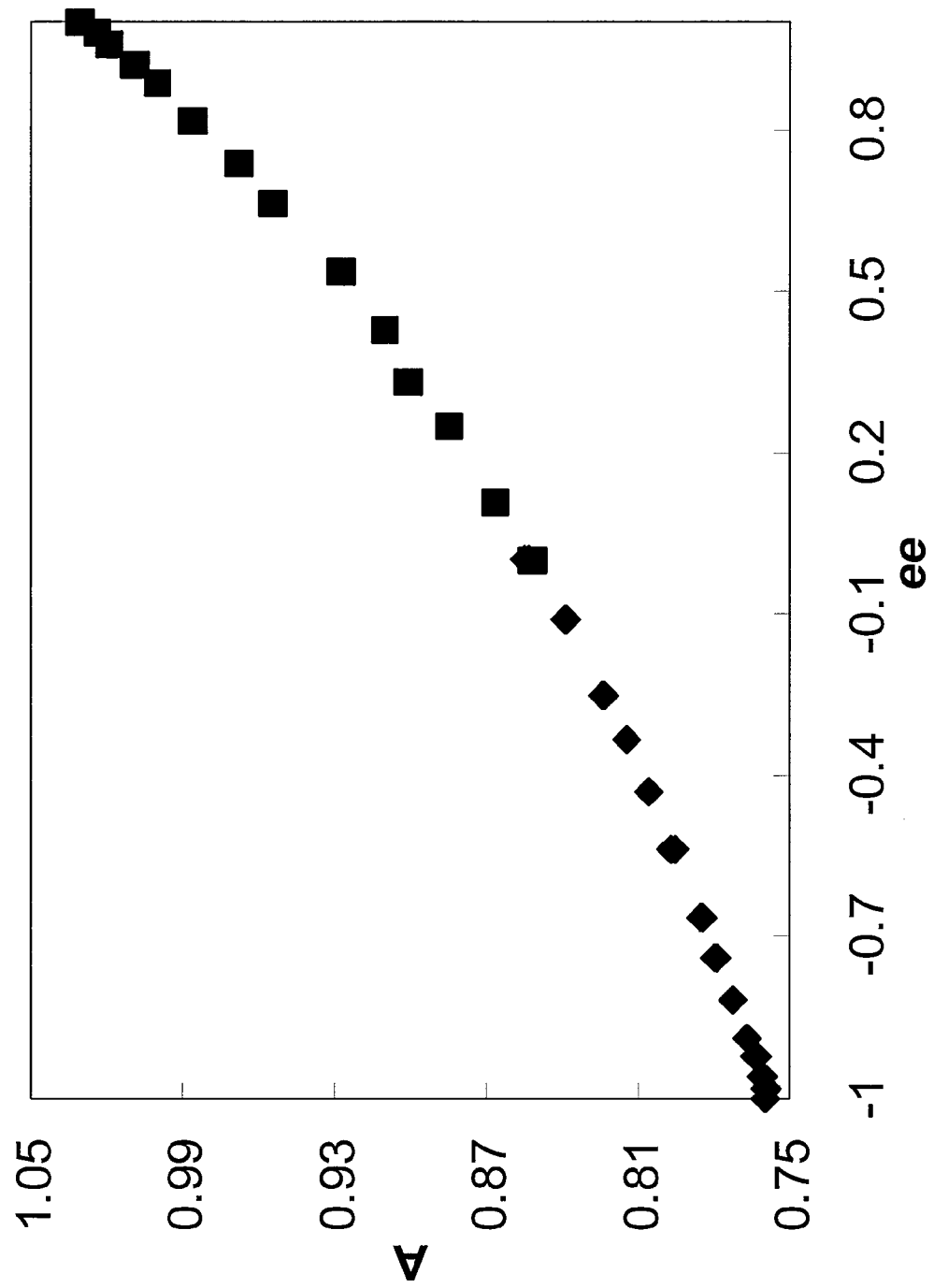
FIG. 8B graphically presents the absorbance change at 520 nm in the ee (of D-PL) range from −1 to 1. Red diamonds: ee from −1 to 0; blue square: ee from 1 to 0. Matched UV-vis cuvettes were used in the measurements.

Two ensemble solutions were prepared with PV (149 μM), Compound (S,S)-2 (0.510 mM) and either D- (solution A) or L-PL (solution B) at 3.00 mM. Solution A was incrementally titrated into B until ee reached 0, while the UV-vis spectrum was recorded after at least 3 min to allow the system reaching equilibrium. (FIG. 8A). The titration was repeated with B adding into A to complete the ee range from −1 to 1. Absorbance change was plotted against ee at 520 nm (FIG. 8B).

Example 7

Determination of the Concentration and ee of an Unknown PL Sample

Figure 9A:
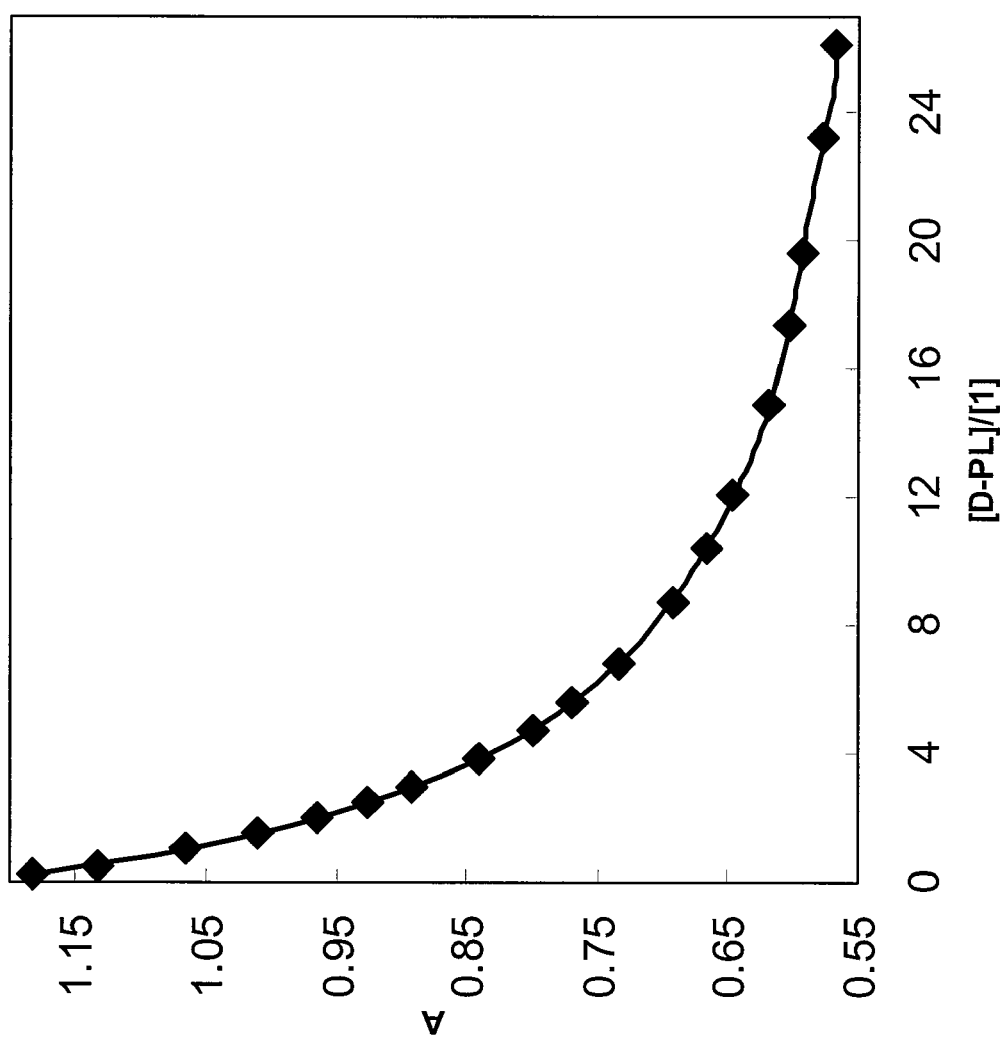
FIG. 9A presents absorbance change at 520 nm of PV (149 µM) and Compound 1 (0.575 mM) in 75% methanolic aqueous solution buffered with 10 mM HEPES at pH 7.4 with increasing concentration of D-PL. The experimental data was fitted empirically to a polynomial equation: $y=3E-08x^6-3E-06x^5+0.0001x^4-0.0022x^3+0.0245x^2-0.164x+1.2123$ ($R^2=1$). The absorption data of unknown PL samples with the indicator-displacement ensemble containing achiral receptor Compound 1 were input to the equation above, which was solved in Methamatica® 5 to afford the overall concentration of PL in the sample.
Figure 9B:
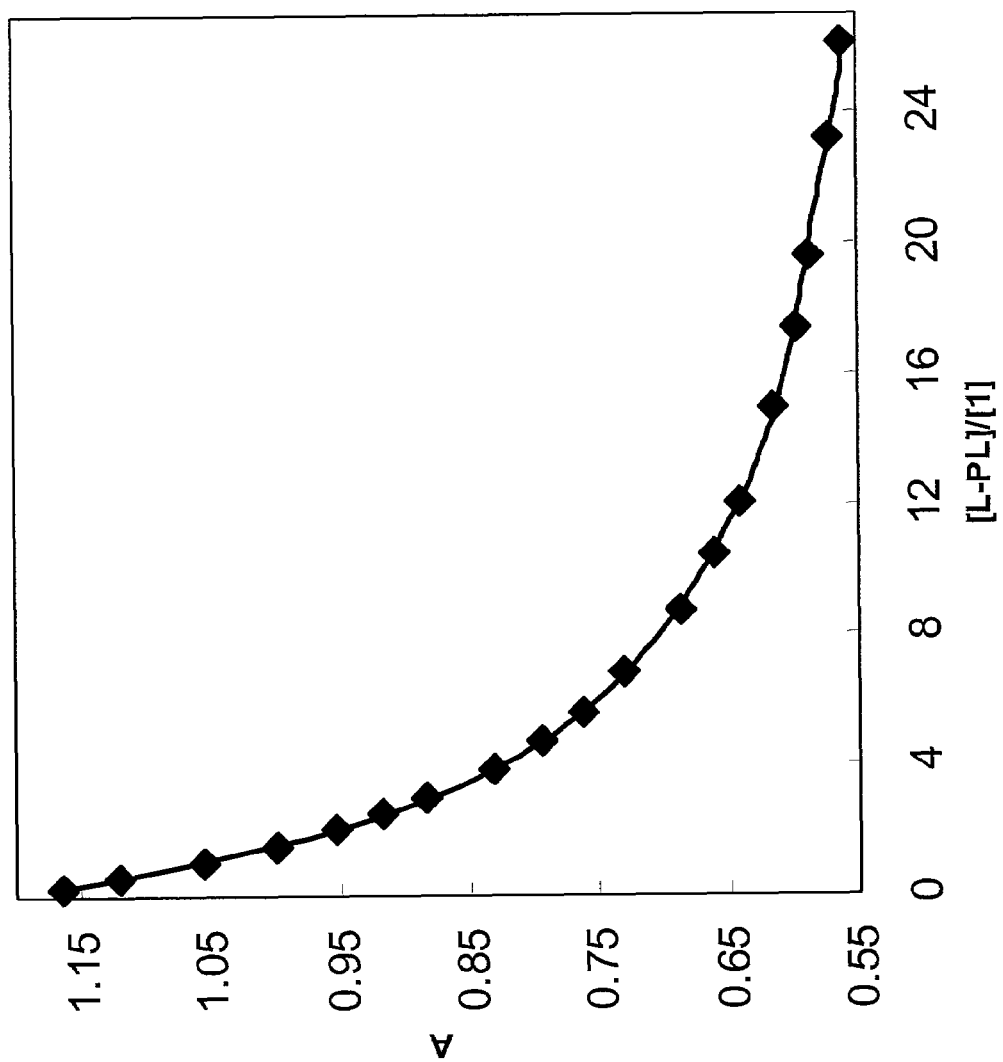
FIG. 9B was created in same manner as FIG. 8A, but with L-PL. The empirical fitting equation is: $y=3E-08x^6-3E-06x^5+0.0001x^4-0.0021x^3+0.0236x^2-0.1592x+1.1959$ ($R^2=1$). The absorption data of the unknown PL sample were input to the equation above to afford another overall concentration.

A PL sample of unknown concentration and ee in the default buffer (0.5 mL) was added in a 5.0 mL volumetric flask containing PV (149 μM) and Compound 1 (0.575 mM). The absorbance at 520 nm was recorded after at least 3 min to allow the system to reach equilibrium. The overall concentration was extracted from calibration curves of A vs. PL concentration (FIG. 9) at 520 nm. The same sample (0.5 mL) was added in another solution containing PV (149 μM) and Compound (S,S)-2 and diluted to 5.0 mL. The absorbance at 520 nm was recorded after at least 3 min and input into Eq. 3. The polynomial equation was solved in Mathematica® to afford the ee of the sample.

Although only exemplary embodiments of the invention are specifically described above, it will be appreciated that modifications and variations of these examples are possible without departing from the spirit and intended scope of the invention.

Example 8

Design of Enantioselective Receptors

Figure 10:
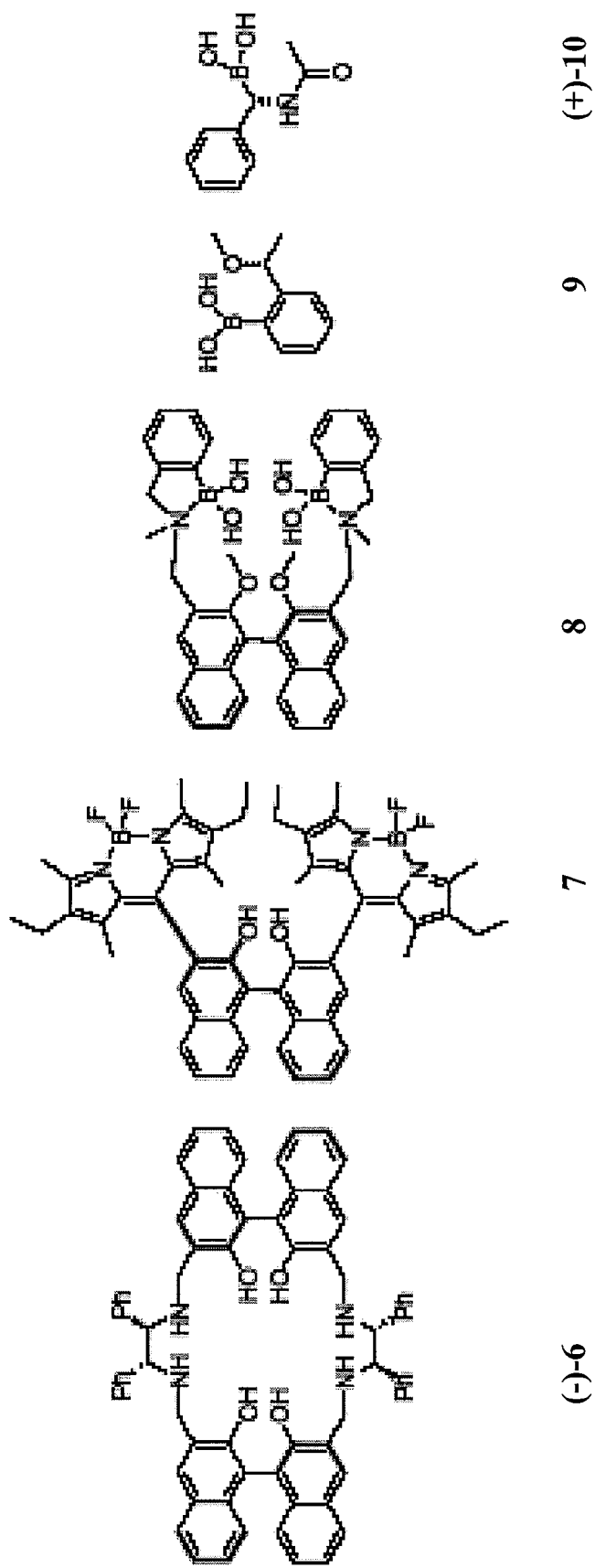
FIG. 10 illustrates some enantioselective chemosensors for various analytes that may be used in connection with specific embodiments of the present invention and that may be detected through fluorescence spectroscopy (compounds (−)-6, 7, and 8), or proton nuclear magnetic resonance spectroscopy (NMR) (9 and 10).

In many reported boronic acid receptors (e.g. compound 8), neighboring tertiary amino groups were installed in proximity of boron atoms. Such amino groups were postulated to accelerate the association equilibria with their substrates, by serving as proton shufflers, or by modulating the thermodynamics of the association as Lewis bases for the boron atoms. It was expected that the nitrogen atom coordinates with the electron-deficient boron atom to form a relatively rigid 5-member-ring structure, as drawn for compound 8 in FIG. 10. Notwithstanding recent debate about the strength of the BN interaction, and whether the bond remains intact in protic media, it was postulated that if stereogenic centers were installed in the vicinity of the postulated B—N bond in the receptor, the stereocenters would impart enantioselectivity to the association between the receptor and enantiomeric substrates. Hence, the chiral receptors 15-21 were devised and synthesized.

Scheme 2. Synthesis of 2-methylpyrrolidinyl phenylboronic acids with reductive amination.

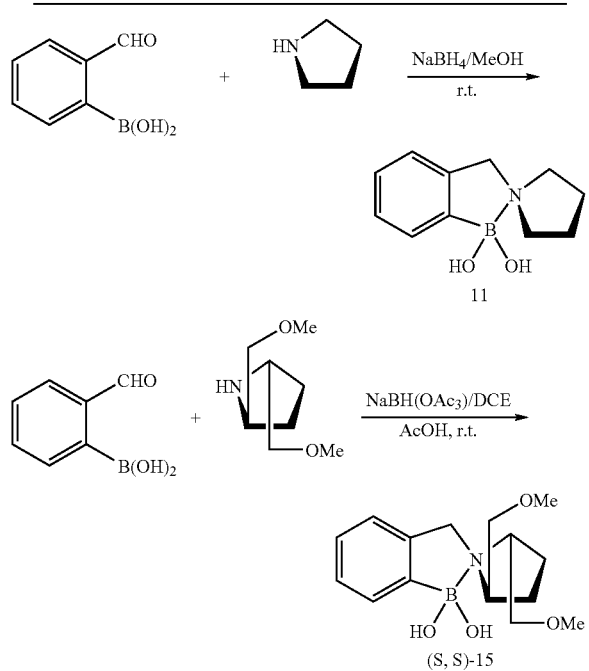

Synthesis. Boronic acid receptors 11-21 were prepared through reductive amination between o-formyl arylboronic acids and various pyrrolidine-based secondary amines (Scheme 2). For the secondary amines without α-substituents, such as pyrrolidine or piperidine, the reductive amination was carried out smoothly with Schiff base formation in methanol followed by reduction with NaBH$_4$. When α-substituted secondary amines were used, the reduction was performed with NaBH(OAc)$_3$ to ensure a selective reduction of the iminium ions. The products were purified with alumina chromatography with satisfying yields (usually more than 70%).

Example 9

Fluorescence Indicators

Figure 11:
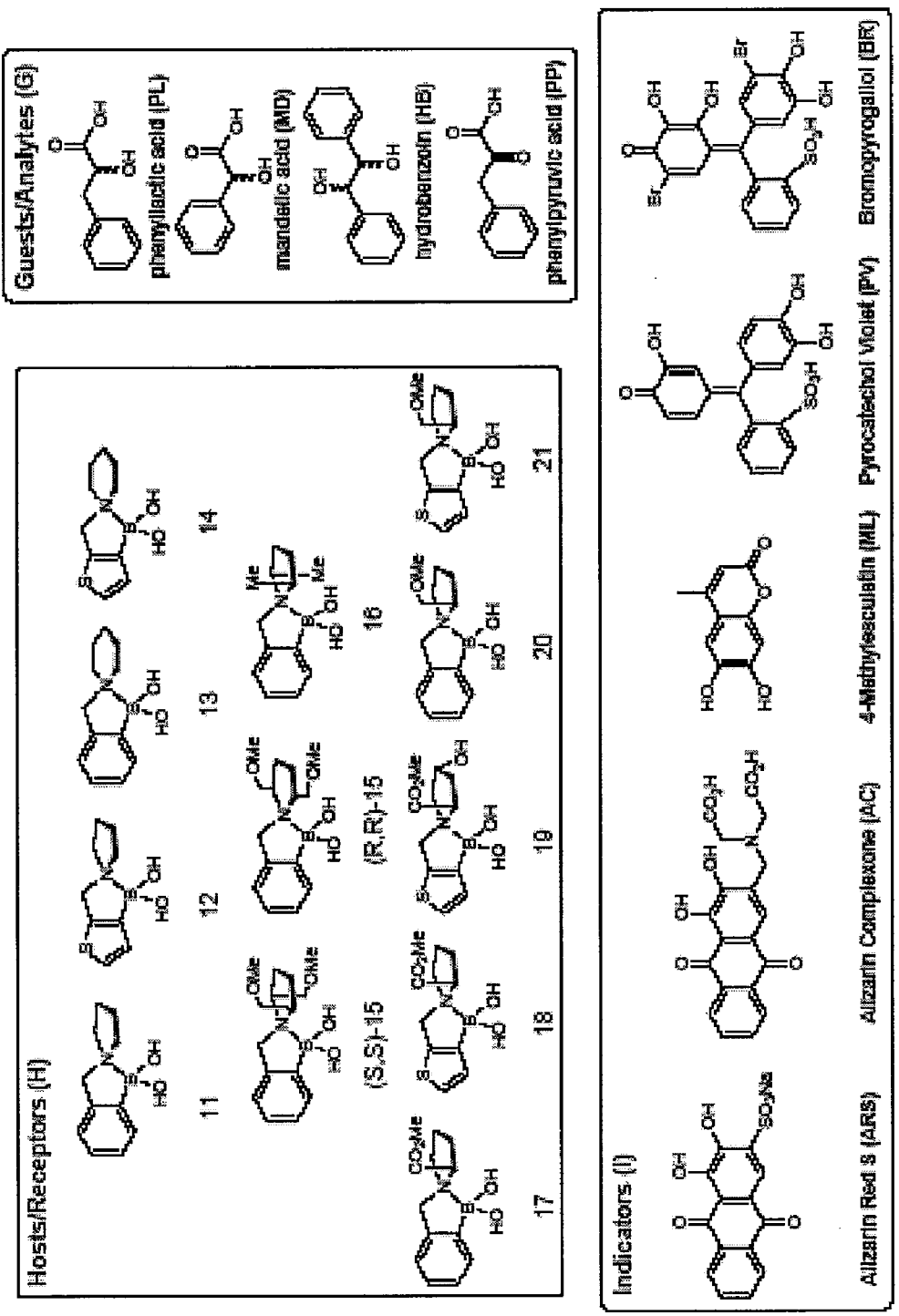
FIG. 11 illustrates structures of hosts/receptors (H), indicators (I), and selected guests/analytes (G) according to the present invention, in which receptor structures are drawn with presumptive B—N bonds.
Figure 12:
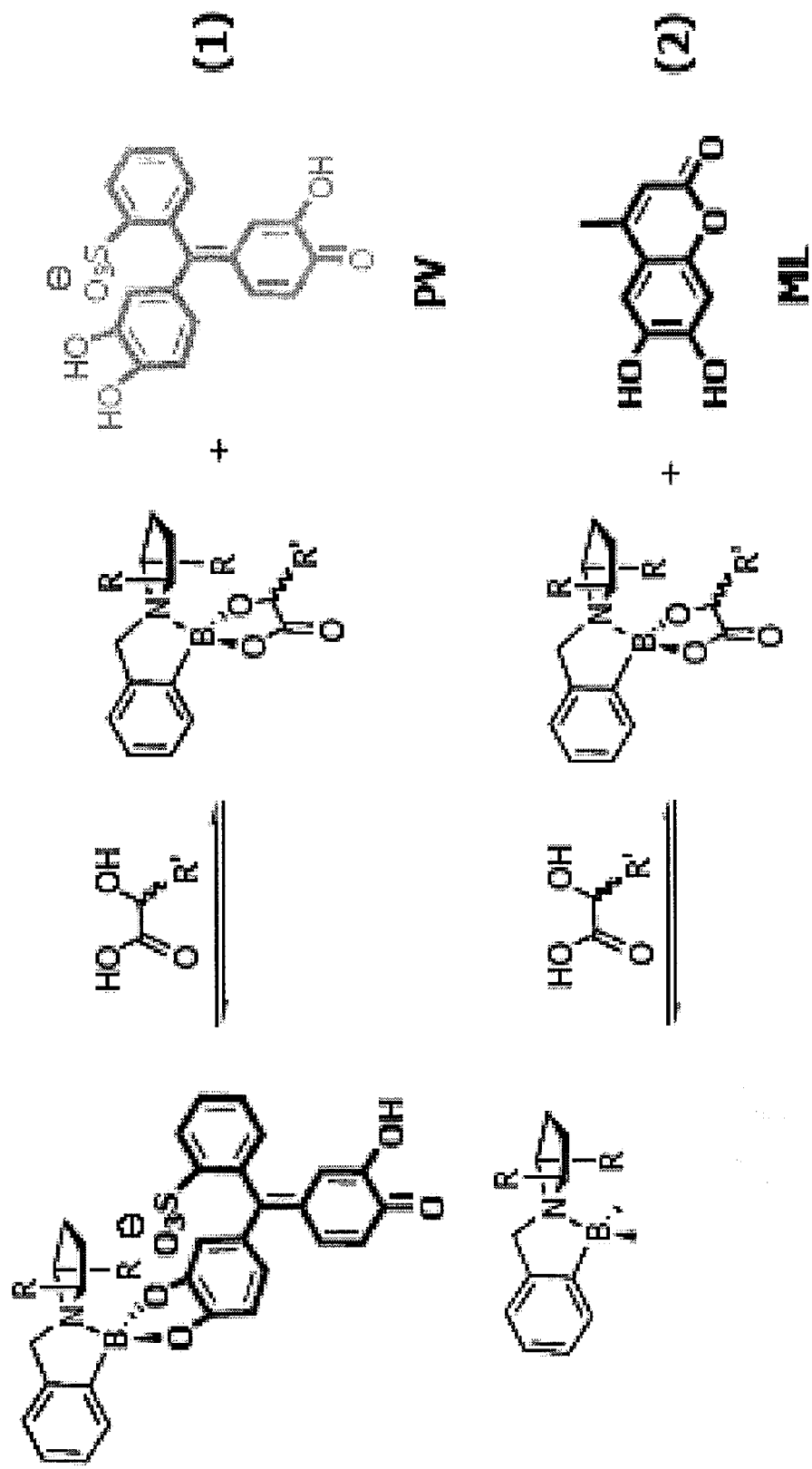
FIG. 12 illustrates enantioselective indicator-displacement assays in accordance with the teachings of the present invention for α-hydroxycarboxylates based upon (1) a colorimetric indicator (PV) and (2) a fluorescent indicator (ML).

The foregoing examples described the enantioselective associations between receptor (S,S)-15 and various α-hydroxycarboxylates. With PV serving as a colorimetric indicator (FIG. 11), the assay was successfully applied in simultaneous determination of concentrations and ees of unknown PL samples. In those measurements, the determined ees had an average of 15% error from the actual values. The main objective of this study was to optimize the protocols to improve both the accuracy and sensitivity of the assay.

Figure 13:
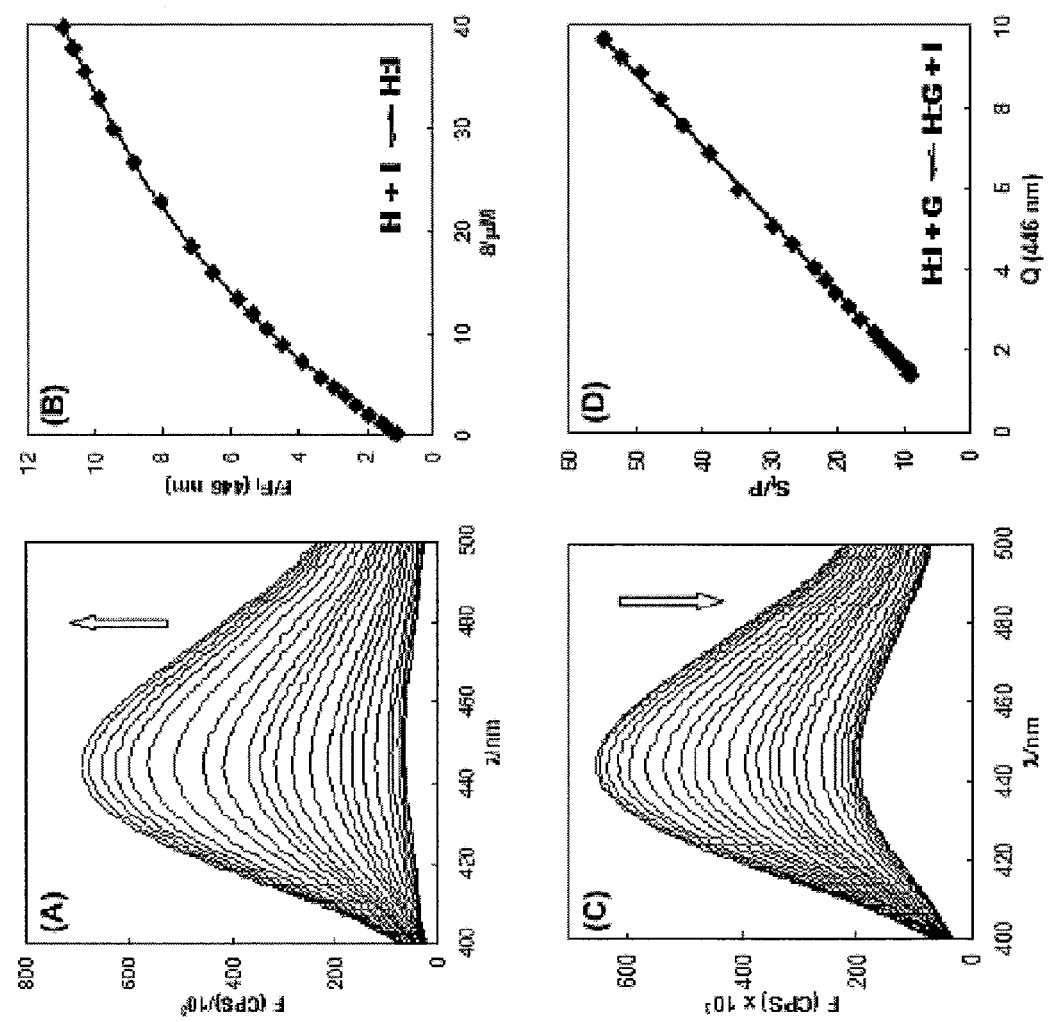
FIG. 13A illustrates fluorescence spectra of ML (3.6 mM) in 75% methanolic aqueous solution buffered with 10 mM HEPES at pH 7.4 (default buffer) in the presence of 0-40 mM 13. Fluorescence intensity (F) is shown as counts per second (CPS).
FIG. 13B illustrates curve fitting of relative fluorescence intensity vs. receptor (13) concentration at 446 nm (excited at 362 nm), $F_f$—fluorescence intensity of the unbound indicator ML.
FIG. 13C illustrates fluorescence spectra of ML (3.6 mM) and 13 (31.9 mM) in the default buffer in the presence of 0-1.5 mM of L-PL.
FIG. 13D illustrates an $S_f/P$ vs. Q plot from the competitive fluorimetric method, derived from the competitive spectrophotometric method,[10] with data taken at 446 nm.

In order to devise assays with higher sensitivities and improved accuracy, fluorescent indicators were examined. The indicator 4-methylesculetin (ML, FIG. 11) was found to undergo a large fluorescence intensity enhancement upon binding with boronic acid receptors such as 13 and (S,S)-15. At pH 7.4 in a 75%/25% methanol/H$_2$O solution, the emission of ML was largely suppressed by the photo-induced electron transfer (PET) process from the hydroxyl groups to the coumarin moiety. Therefore, the free ML showed relatively weak fluorescence. Upon binding with boronic acid receptors, the electron deficient boron atoms raised the oxidation potential of the hydroxyl groups on ML, so that the presumptive PET process was thermodynamically disfavored. Thus, when binding with compound 13, the fluorescence from the coumarin moiety in the complex had at least a 10-fold enhancement over the free indicator (FIGS. 13A and 13B). Upon addition of PL, the fluorescence intensity decreased due to the competitive binding of PL to the receptors that released the indicator into solution (FIG. 13C). The association constants between the receptors and ML were determined through the 1:1 binding isotherms (FIG. 13B, see supporting information). The affinities of the receptors to PL were determined with a traditional competitive spectrophotometric method (FIG. 13D). The affinity data are listed in Table 5.

TABLE 5

Association constants (K/10$^3$ M$^{-1}$) of boronic receptors (13, (S,S)-15) with indicator ML and D/LPL[a]

|  | ML | D-PL | L-PL |
| --- | --- | --- | --- |
| 13 | 24.92 ± 0.07 | 4.50 ± 0.09 (4.38 ± 0.05) | 4.56 ± 0.08 (4.39 ± 0.06) |
| (S,S)-15 | 30.19 ± 1.55 | 4.35 ± 0.07 (4.27 ± 0.24) | 10.86 ± 0.03 (10.45 ± 0.10) |

[a]Measured via 1:1 binding isotherms or a competitive fluorimetric method in the default buffer (FIG. 3, footnote). Association constants obtained from iterative curve fitting are shown in the parentheses for comparison.

Figure 14:
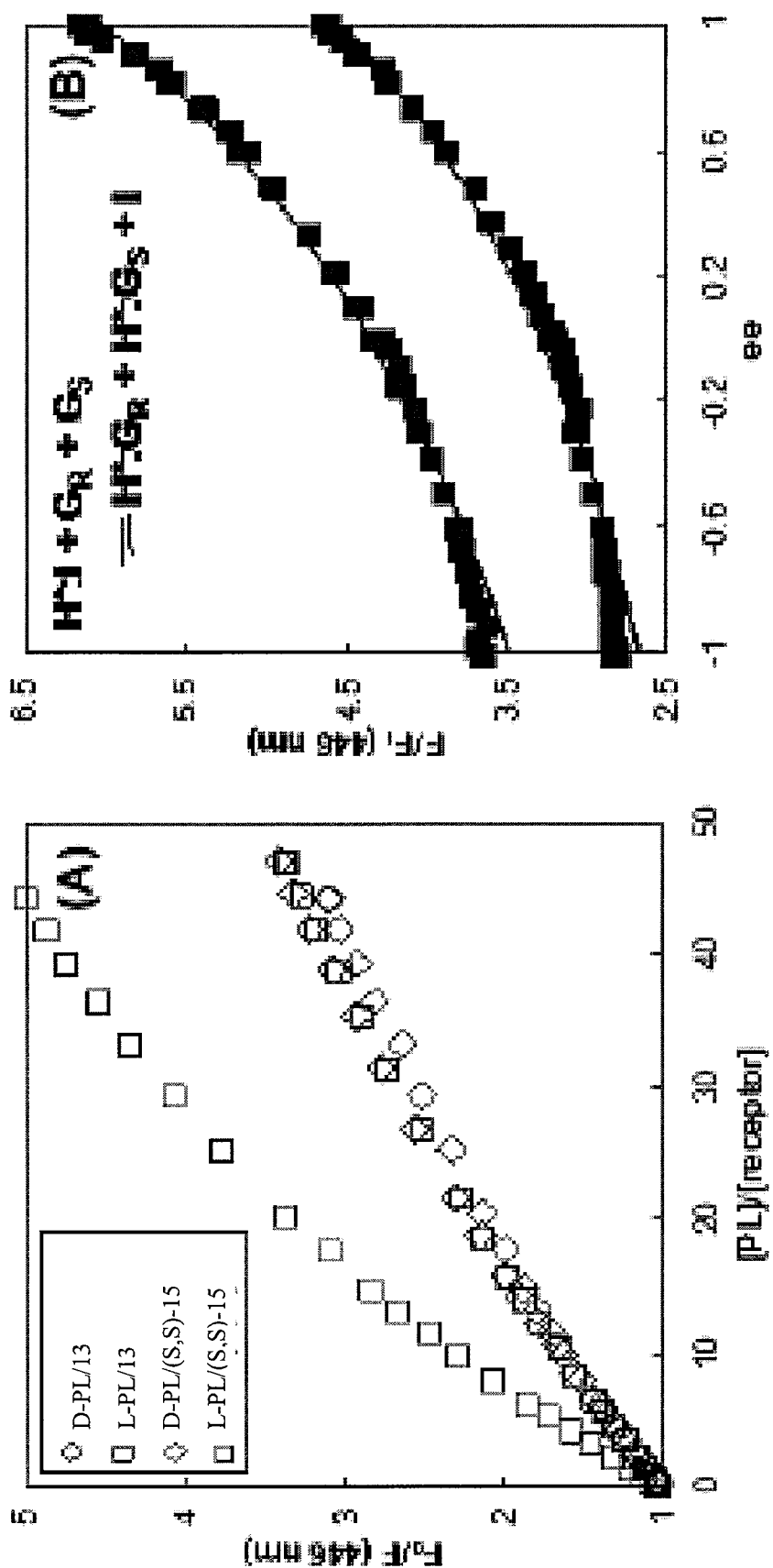
FIG. 14A illustrates fluorescence quenching profiles at 446 nm of ML (3.6 mM) and receptors (S,S)-15 (34 mM), or 13 (31.9 mM) in the default buffer (footnote, FIG. 12) with increasing concentration of D- or L-PL, displayed in a Stem-Volmer format. Data are shown as the averages of two measurements. F—Fluorescence intensity (CPS); $F_0$—Fluorescence intensity (CPS) at the inception.
FIG. 14B illustrates relative fluorescence intensity change at 446 nm of ML (3.6 mM), receptor (S,S)-15 (34 mM), and analyte solutions upon increasing ee of D-PL. $F_f$-fluorescence intensity (CPS) of the free indicator at the designated concentration (see the next section); red: $[G]_t=676$ mM; blue: $[G]_t=1.2$ mM. The solid lines are theoretical curves resulted from iterative data fitting. The association constants extracted from the fitting are (averages from two total concentrations): $K_R=(3.39\pm0.03)\times10^3$ M$^{-1}$; $K_S=(9.79\pm0.48)\times10^3$ M$^{-1}$.

The fluorescence displacement profiles of PL with the achiral (13) and chiral ((S,S)-15) receptors are shown in FIG. 14A. As expected, with chiral receptor (S,S)-15, the stronger associating PL enantiomer (LPL) resulted in a more effective fluorescence quenching event than D-PL; while their fluorescence displacement profiles were virtually identical with achiral receptor 13. The ee-dependent fluorescence quenching (of an indicator-receptor ensemble) profiles of PL at two different total substrate concentrations are displayed in FIG. 14B. The profile derived from the larger total concentration of the guest (1.2 mM, blue) showed an overall more effective fluorescence quenching with an otherwise similar shape. The fluorescence intensities were growing with the increasing ee of the weaker associating enantiomer—D-PL. The slope of the emission intensity as a function of ee (dF/dee) was greater when the ee of D-PL became larger (FIG. 14B), because the concentration change of the stronger associating enantiomer ($\Delta$[L-PL]) had a more pronounced effect in modulating fluorescence intensity when its concentration ([L-PL]) was relatively small than vice versa. Through this study, an enantioselective indicator-displacement assay for PL was established based upon enantioselective associations between receptor (S,S)-15 and D/L-PL, and the utilization of the fluorescent indicator ML.

Example 10

Mathematical Analysis of Solution Equilibria

Because the enantioselective fluorescent indicator displacement assay follows solution equilibria (Scheme 1), a relationship between the ee of a sample and the fluorescence intensity can be established. One goal was to discover if iterative curve fitting of the $F/F_I$ vs. ee curve would give a more accurate ee assay than previously reported.

The fluorescence intensity F is related to both the free and bound indicator I and HI via eq. 1 ($I_0$—the intensity of the excitation source; $\phi$—fluorescence quantum yield; $\epsilon$—molar absorptivity at the excitation wavelength; b—path length).58 With $F_I$ defined as the fluorescence intensity from the free indicator ($F_I \equiv k_I b[I]_t$), eq. 10-1 is converted to eq. 10-2. When a mixture of enantiomeric guests is present, the concentrations of all the solution species are defined by three solution equilibria equations 10-3 to 10-5. Other restricting factors include mass balances for the receptor (H), the indicator (I), and the analyte ($G_R$, $G_S$), as well as the definition of ee (eq. 10-6 to 10-9). By rearranging the equations with the aid of the commercial software Mathematica,59 the concentrations of all the solution species ([I], [HI], [$HG_R$], [$G_R$], [$HG_S$], [$G_S$], and [H]) can be expressed as functions of measurable parameters ([H]t, [I]t, [G]$_t$, KI, $K_R$, $K_S$, and n). When these symbolic expressions are introduced into eq. 10-6, an implicit $F/F_I$ vs. ee relationship is given in eq. 10-10. Other parameters can be independently determined through 1:1 binding isotherms (KI, n), competitive binding methods ($K_R$, $K_S$), gravimetric measurements ([H]$_t$, [I]$_t$), and achiral indicator-displacement assays ([G]$_t$), respectively. If $K_R$ equals $K_S$, as in a displacement assay with an achiral host, eq. 10-10 can be rearranged to give the typical equation for the competitive spectrophotometric method (see supporting information). The correlation between the traditional approach and the present analysis provides validation for the $F/F_I$ vs. ee relationship shown in eq. 10-10.

$$F = k_I b[I] + k_{HI} b[HI] (k \equiv 2.3 I_0 \phi \epsilon) \quad (1)$$

$$F/F_I = [I]/[I]_t + n[HI]/[I]_t (n = k_{HI}/k_I, F_I = k_I b[I]_t) \quad (2)$$

$$[HI] = K_I[I][H] \quad (3)$$

$$[HG_R] = K_R[G_R][H] \quad (4)$$

$$[HG_S] = K_S[G_S][H] \quad (5)$$

$$[H] + [HI] + [HG_R] + [HG_S] = [H]_t \quad (6)$$

$$[I] + [HI] = [I]_t \quad (7)$$

$$[G_R] + [G_S] + [HG_R] + [HG_S] = [G]_t \quad (8)$$

$$ee_R = \frac{([G_R] + [HG_R]) - ([G_S] + [HG_S])}{[G]_t} \quad (9)$$

$$\frac{(F/F_I - 1)[I]_t}{n-1} + \frac{(F/F_s - 1)}{K_s(n - F/F_s)} + \frac{K_R[G]_t(1 - ee_s)(1 - F/F_s)}{2[(F/F_I)(K_S - K_R) - (nK_S - K_R)]} + \frac{K_R[G]_t(1 + ee_s)(1 - F/F_s)}{2[(F/F_I)(K_R - K_S) - (nK_R - K_S)]} = [H]_t \quad (10)$$

When all the measurable parameters (KI, n, $K_R$, $K_S$, [H]$_t$, [I]$_t$, [G]$_t$) were introduced into eq. 10-10, calibrating curves of $F/F_I$ vs. ee with given [G]$_t$ concentrations were generated. Although the calculations were very close, they did not always sufficiently reproduce the experimental data for a good ee determination. This is largely due to the fact that the parameters are necessarily determined under somewhat different conditions. Fluctuations in room temperature, the power supply of the fluorimeter, and the sensitivity of the detection system, etc., over the time when the measurements of the parameters were conducted contributed to the discrepancy between the calculated and experimental $F/F_I$ vs. ee data. Therefore, a method enabling iterative data fitting of experimental $F/F_I$ vs. ee curves by adjusting $K_R$ and $K_S$, with secondary consideration of other parameters was sought. Curve fitting of the $4^{th}$ order polynomial $F/F_I$=f(ee) relationship (eq. 10-10) presented a daunting task. Even traditional competitive binding curves without the ee consideration had not been previously fit iteratively. However, direct determination of binding constants from competitive binding curves through iterative data fitting may be feasible with the use of commercial software.

As a start, the nonlinear function A=f([G]$_t$) in Scheme 1 was studied without the ee consideration. The absorbance was correlated to indicator concentrations through Beer's Law (eq. 10-11). The [I] and [HI] values were dictated by solution equilibria between H, I and G (eqs. 10-12 and 10-13), with restrictions from their mass totals (eqs 10-14-10-16). By rearranging eqs 10-12 and 10-14, [I] and [HI] were expressed as functions of [H], and subsequently these functions were introduced into the Beer's Law eq. 10-11 to afford eq. 10-17 in the form of A=f([H]). Similarly, [HG] was expressed as a function of [H] by rearranging eqs 10-13 and 10-16. The symbolic values of [HI] and [HG] in terms of [H] were introduced into the mass balance of [H]$_t$ (eq. 10-15) to afford a cubic equation in [H] (eq. 18). At this point, all the parameters in eqs 10-17 and 10-18, except for $K_G$ that was to be determined, were known from gravimetric means ([H]$_t$, [I]$_t$, [G]$_t$) or previous measurements ($\epsilon_I$, $\epsilon_{HI}$, $K_I$).

Actual curve fitting was achieved by the nonlinear least squares curve fitting module of the commercial software Origin, that ran a brief user-defined function compiled with the LabTalk computation language integrated in the software package. The compiled function had a two-step iterative cycle. First, an arbitrarily estimated value was assigned to $K_G$. [H] was subsequently obtained from solving the cubic eq. 10-18 based on the Newton-Raphson method. Because of the multiplicity of the roots from a cubic equation, it should be stressed that a judicious choice of the initial value of [H] ([H]$_{ini}$ for the Newton-Raphson method) is pivotal to the success of obtaining a reasonable calculated value of [H]. Second, the obtained [H] was introduced to eq. 10-17 to afford a calculated absorbance (A) value. This value was compared with the measured A value by the curve-fitting module to evaluate the quality of the initially assigned $K_G$.

The program then generated a new, and usually superior, value for $K_G$ based upon the Levenberg-Marquardt algorithm, and the above process was repeated until the best value of $K_G$ was found.

| Beer's Law: | $A = \epsilon_I b[I] + \epsilon_{HI} b[HI]$ | (10-11) |
|---|---|---|
| Solution equilibria: | $[H_I] = K_I[I][H]$ | (10-12) |
| | $[HG] = K_G[G][H]$ | (10-13) |
| Mass balance: | $[I] + [HI] = [I]_t$ | (10-14) |
| | $[H] + [HI] + [HG] = [H]_t$ | (10-15) |
| | $[G] + [HG] = [G]_t$ | (10-16) |
| Beer's Law: | $A = \epsilon_I[I]_t/(1 + K_I[H]) +$ | (10-17) |
| | $\epsilon_{HI} b K_I[H][I]_t/(1 + K_I[H])$ | |
| | $K_I K_G[H]^3 + (K_I + K_G +$ | |
| | $K_I K_G[G]_t - K_I K_G[H]_t)[H]^2 + (1 +$ | (10-18) |
| | $K_I[I]_t + K_G[G]_t -$ | |
| | $K_I[H]_t - K_G[H]_t)[H] - [H]_t = 0$ | |

Figure 15:
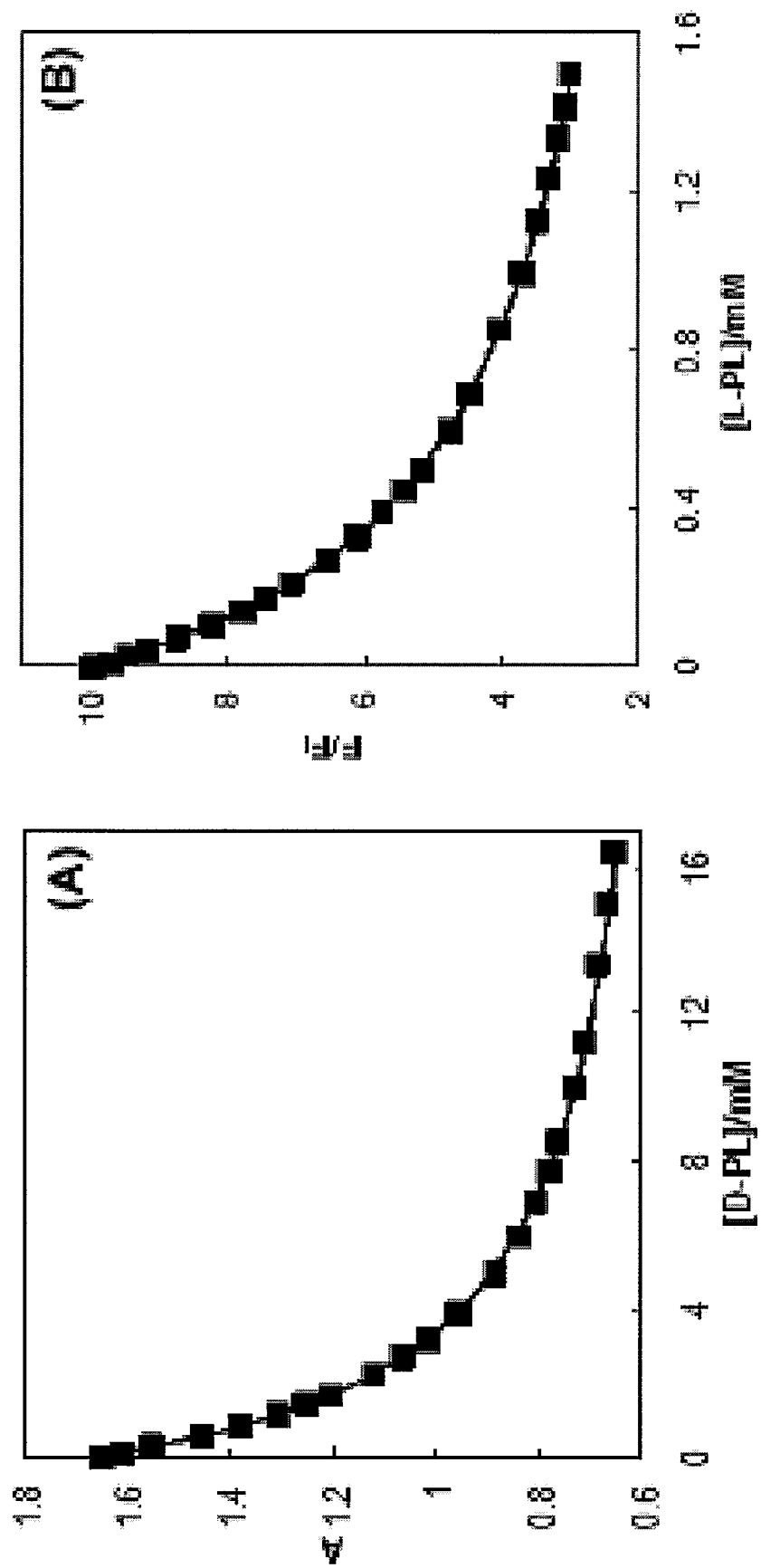
FIG. 15A illustrates the absorbance at 520 nm of PV (149 mM) and receptor (S,S)-15 (0.51 mM) in the default buffer (FIG. 3, footnote) with increasing concentration of D-PL; solid line: theoretical curve from iterative fitting in Origin with a user defined function.
FIG. 15B illustrates the fluorescence intensity (F/F$_f$) of ML (3.6 mM) and receptor 13 (31.9 mM) in the default buffer with increasing concentration of L-PL; solid line: theoretical curve from iterative fitting in Origin with a user defined function.

The above algorithm can be applied generally in cases involving two interdependent equilibria. For indicator-displacement studies, there are usually 6 parameters besides the variables A and $[G]_t$—$K_G$, $K_I$, $[H]_t$, $[I]_t$, $\epsilon_I$, and $\epsilon_{HI}$—that can be adjusted to obtain a satisfying curve fitting (i.e. $R_2>0.99$). The following procedure was established to restrict the variations of the parameters in order to afford a reasonable and reproducible $K_G$. $[H]_t$, $[I]_t$, which were obtained gravimetrically, and $K_I$, which was independently determined from a 1:1 binding isotherm, were treated as fixed parameters. The extinction coefficients $\epsilon_I$, and $\epsilon_{HI}$ were dependent on experimental conditions (temperature, background absorption, etc.). Therefore, they were allowed for variation. Various data sets were then fit successfully with this method, with one example shown in FIG. 15A. Selected results are shown in parallel with association constants determined by the traditional competitive spectrophotometric method in Table 9. A similar approach was applied to data sets based on fluorescence measurements (one example in FIG. 15B), and the results are shown in Table 5. The fitting quality exemplified in FIG. 15, the accuracy displayed in Tables 5 and 9, the generality to multiple equilibria problems, and the ease of operation, make this approach a preferred embodiment of the invention.

Next, the algorithm targeting iterative curve fitting of an A or $F/F_I$=f(ee) calibration curve in an enantioselective indicator-displacement assay was developed in a similar manner, but with one step of higher complexity (see supporting information). In an assay based upon fluorescence, there were 7 parameters besides variables $F/F_I$ and ee: $K_I$, n, $K_R$, $K_S$, $[I]_t$, $[H]_t$, and $[G]_t$ (eq. 10-10). Gravimetric values ($[I]_t$, $[H]_t$, $[G]_t$), $K_I$ and n from a 1:1 binding isotherm, were treated as invariable. Now the data was fit (FIG. 14B) by varying the values of the association constants between the chiral receptor and the enantiomers of the analyte ($K_R$, $K_S$). As a validation to this approach, the association constant values obtained from the fitting of the ee curves (see captions of FIGS. 14B and 16D) matched very well (the errors were less than 5% as shown in Table 5) to the values determined from both the traditional competitive binding method and the iterative fitting of competitive binding curves with enantiomerically pure substrates (Tables 5 and 9).

Example 11

Determination of ee in Phenyllactic Acid Samples via Fluorimetry

To use the $K_R$ and $K_S$ obtained from the iterative fitting of $F/F_I$ vs. ee curves for determination of ees of unknown PL samples eq. 10-10 was solved. It was found that the association constants obtained by iteration gave more accurate results than those extracted from competitive binding curves with enantiomerically pure PLs. This may be because some of the factors affecting the accuracy of the $K_R$ and $K_S$ values, such as the variation of ionic strength and subtle volume changes during the measurements, are kept to a minimum in the $F/F_I$ vs. ee measurements. As more and more $F/F_I$ vs. ee data at different concentrations are accumulated, the average values of $K_R$ and $K_S$ obtained with different total analyte concentrations will move closer to their true values.

From the available $F/F_I$ vs. ee data (FIG. 14B), 10 data points (5 for each concentration) were randomly selected and designated as samples with unknown ees. The curves were fit with the remaining data points to obtain two sets of $K_R$ and $K_S$ values. The average $K_R$ (3394 $M^{-1}$) and $K_S$ (9791 $M^{-1}$) were used in conjunction with other parameters ($K_I$=31,744 $M_{-1}$, $[I]_t$=3.6×10$^{-6}$ $M^{-1}$, $[H]_t$=34×10$^{-6}$ $M^{-1}$, $[G]_t$=676×10$^{-6}$ $M^{-1}$ or 1.2×10$^{-3}$ $M^{-1}$, and n=21.3) in eq. 10-10 to calculate the ees of the unknown samples based on their fluorescence intensity. The determined ee values were in good agreement with the actual numbers (Table 6). By using fluorimetry and $K_R$ and $K_S$ values determined from the $F/F_I$ vs. ee curves, the average error was found to be 7%.

TABLE 6

Determination of ees of 10 PL samples by fluorimetry.

| | Sample No. | | | | |
|---|---|---|---|---|---|
| | 1 | 2 | 3 | 4 | 5 |
| Actual ee ($[G]_t$ = 676 μM) | 0.90 | 0.33 | 0 | −0.67 | −1.00 |
| Determined ee | 0.92 | 0.26 | −0.13 | −0.72 | −0.89 |
| Actual ee ($[G]_t$ = 1.2 mM) | 0.98 | 0.21 | −0.03 | −0.38 | −0.98 |
| Determined ee | 1.02 | 0.18 | −0.09 | −0.26 | −0.57 |

Example 12

Displacement with Other Substrates

To extend the analyte range of techniques of the invention, the affinities between different receptors, indicators and guest molecules other than PL were determined via absorption spectroscopic method. Among all the indicators studied, alizarin red S (ARS) has the largest affinity for the receptors. Generally, the affinities of indicators to a given receptor follow the sequence ARS>AC>ML≈BR>PV (Table 7). The visible absorption maxima of ARS, AC, and PV undergo dramatic shifts upon binding with the receptors (Table 7), which establish them as effective colorimetric indicators. BR also undergoes a large absorption maxima shift when associating with the receptors. However, the extinction coefficient of its bound form ($\epsilon_{HI}$) is too small to enable an actual color change. ML absorbs in the UV region, and its application as a fluorescent indicator was described in the previous section. In terms of receptors, except for the proline-derived compounds (17-21) which have no measurable associations to any indicators except ARS, all the others have comparable affinities to the indicators (Table 8).

The association properties of receptors 11, 12, (S,S)-15, and 16 with selective substrates were studied with indicator-displacement assays. PV was selected as the indicator, and the association constants are listed in Table 9. Achiral receptors 11 and 12 showed no selectivity between enantiomers of the guest molecules as required by first principles of stereochemistry. The receptors had stronger affinities toward ahydroxycarboxylates (e.g. PL and mandelic acid—MD) than the vicinal diol hydrobenzoin (HB), which is consistent with other results.[29,64] Chiral receptor (S,S)-15, and compound 16 to a lesser extent, displayed enantioselectivities toward both a-hydroxycarboxylates and the diol HB. Another diol studied, 3,4-butanediol, showed no measurable affinity to 13. Other bifunctional substrates that were investigated include b-hydroxyacid (3-hydroxybutyric acid), amino acids (tert-leucine), BINOL, amino alcohol (phenylglycinol), and ascorbic acid. Ascorbic acid showed considerable affinity via a very slow equilibrium (the color change occurs during a course of several hours). All other substrates studied do not appear to associate with the boronic receptors.

TABLE 7

Association constants ($K_I/10^3$ $M^{-1}$) of receptor 11 with various indicators and their bathochromic or hypsochromic responses upon association.

| Indicator | ARS | AC | ML | PV | BR |
|---|---|---|---|---|---|
| batho-/hypsochromic shift/nm | 540 → 456 | 525 → 440 | 294 → 364 | 440 → 480 | 565 → 470 |
| $K_I/10^3$ $M^{-1}$ | 50 | $13^2$ | 8.7 | $2.3^2$ | 8.1 |

TABLE 8

Association constants ($K_I/10^3$ $M^{-1}$) of boronic receptors (11-21) with indicator AC$^a$

| Host | 11 | 12 | 13 | 14 | (S,S)-15 | (R,R)-15 | 16 | 17 | 18 | 19 | 20 | 21 |
|---|---|---|---|---|---|---|---|---|---|---|---|---|
| $K_I/10^3$ $M^{-1}$ | 13 | 16 | 48 | 22 | 63 | 61 | 53 | — | 1.8 | 0.94 | 57 | 16 |

$^a$Receptors 12-14 do not associate with AC. Their affinities to indicator ARS are shown in italics instead. b

TABLE 9

Association constants ($K_G/10^3$ $M^{-1}$) of selected receptors with selected substrates (determined via competitive spectrophotometric method) and indicator PV.

| | PV | D-PL | L-PL | R-MD | S-MD | (R,R)-HB | (S,S)-HB |
|---|---|---|---|---|---|---|---|
| 11 | $2.3^a$ | $1.3^a$ (1.3) | $1.3^a$ (1.3) | 0.64 | 0.71 | 0.54 (0.53) | 0.53 (0.50) |
| 12 | 3.0 | 1.6 | 1.6 | 0.90 | 0.93 | 0.42 (0.48) | 0.42 (0.40) |
| (S,S)-15 | $13^a$ | $3.4^a$ (2.9) | $9.6^a$ (8.4) | $2.4^a$ | $3.0^a$ | 0.49 (0.46) | 1.3 (1.3) |
| 16 | 12 | 3.1 | 4.6 | 2.1 | 3.2 | N.D.$^c$ | N.D. |

Selective association constants obtained from direct iterative curve fitting are shown in the parentheses for comparison.
$^c$N.D.: Not determined.

In order to employ the enantioselective binding of (S,S)-15 in a sensing application, a protocol was needed to maximize the sensitivity of the assay to the ee variations of chiral samples. This included the selection of an indicator, a proper concentration for the indicator, and an optimized indicator/receptor ratio. It is ideal to have an indicator with an affinity between that of two competing analytes ($K_G>>K_{I}>>K_{G'}$),9 which are two enantiomers in this example. However, this condition cannot always be easily met. For example, in this example, the analytes' affinities to the receptors were generally weaker than that of the indicators (Table 7, 9). Therefore, the indicator PV was chosen because its affinity to the receptor was the closest to the analytes among all the candidates. In this case, the equilibrium H+I⇌H:I was most sensitive to the competition of the enantiomeric analytes $G_R$ and $G_S$.

Next, for selecting a proper concentration of the indicator, the chiral resolution of an enantioselective indicator-displacement assay at a given analyte concentration and a given wavelength was defined as the absorbance difference between the enantiomers ($DA=|A_R=A_S|$) for the ease of the analysis. DA, the chiral resolution, is a function of $K_R$, $K_S$, $K_I$, $[H]_t$, $[I]_t$, etc., as discussed in the last example. A set of empirical principles was applied for maximizing the assay's chiral resolution ($\Delta A$). When $K_R=K_S$ and $\Delta A=0$, the assay loses its enantioselectivity. Consequently, the primary factor determining the enantioselective response of the assay should be the enantioselectivity of the receptor to the enantiomers of the analyte. The secondary factor is the signal amplifying power ($\epsilon$ or $\phi$) of the indicator, which is proportional to $\Delta A$ (or $\Delta F$ in a fluorescent assay). Therefore, the indicator concentration should be as high as possible within the constraint of Beer's Law in order to maximize $\Delta A$. Finally, the assay's enantioselecting power should increase with increasing concentration of the chiral receptor ($\Delta A \propto [H_t]$). On the other hand, if the indicator is saturated by an excess amount of the receptor, there will be a delayed overall response to the analyte, because the analyte will first interact directly with the free receptor molecules rather than participating in the displacement event. As a result, the overall sensitivity of the assay will be reduced. Through extensive optimization, it was observed that an $[H]_t/[I]_t$ ratio which gives 75-85% indicator saturation in the absence of analytes was best.

Figure 16:
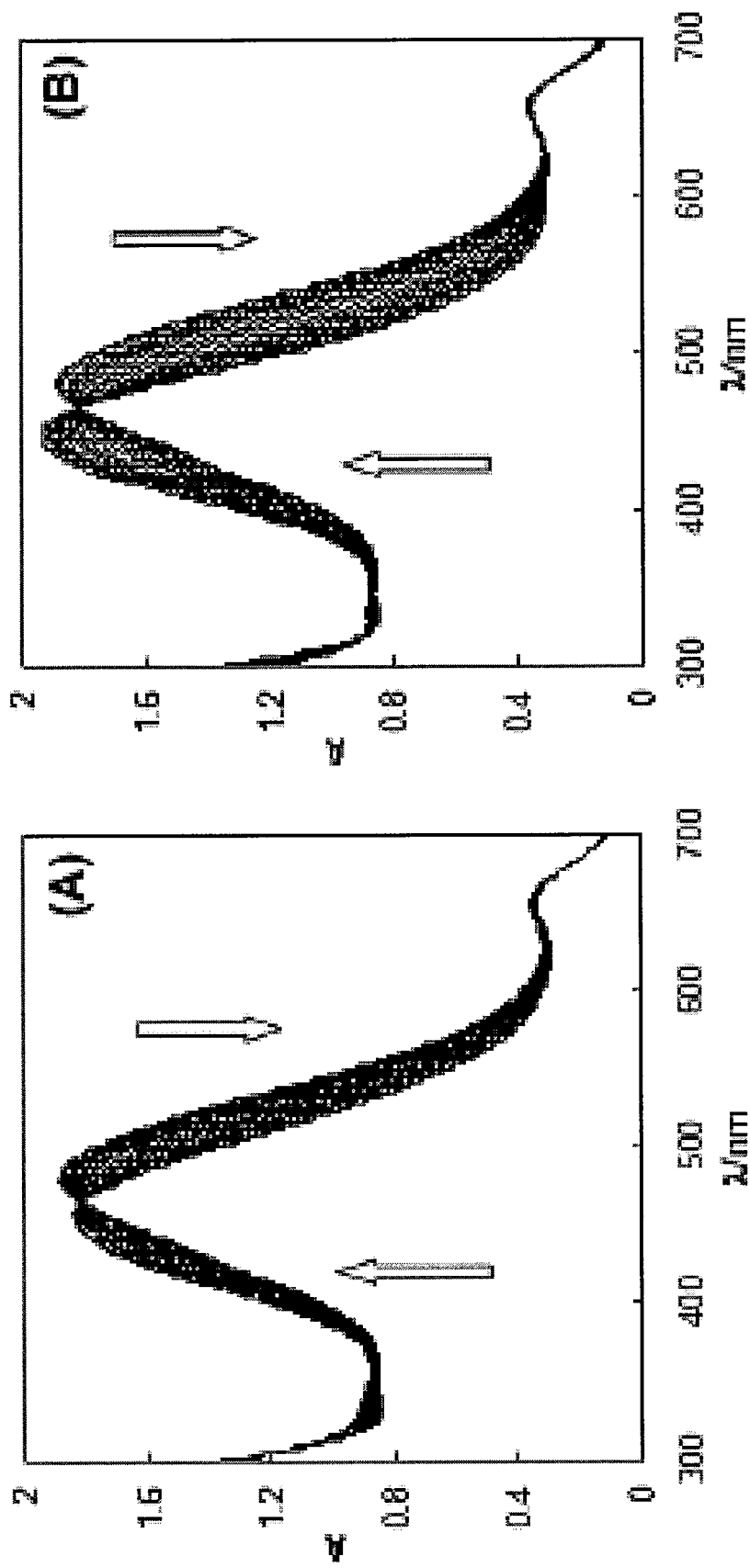
FIG. 16A illustrates an absorption spectra of PV (149 mM) and (S,S)-15 (0.51 mM) in the default buffer (footnote, FIG. 3) in the presence of 0-10 mM of (R,R)-HB.
FIG. 16B illustrates an absorption spectra of PV (149 mM) and (S,S)-15 (0.51 mM) in the default buffer in the presence of 0-10 mM of (S,S)-HB.
FIG. 16C illustrates an absorbance change at 520 nm of PV (149 mM) and receptors (S,S)-15 (0.51 mM), or 11 (0.82 mM) in the default buffer with increasing concentrations of (R,R)- or (S,S)-HB.
FIG. 16D illustrates the absorbance at 520 nm of PV (149 mM), (S,S)-15 (0.51 mM), and HB solutions upon increasing ee of (R,R)-HB. blue: $[G]_t$=15 mM; red: $[G]_t$=7.5 mM. Solid lines are theoretical curves generated from iterative data fitting. The association constants extracted from the fittings are (the average from two total concentrations): $K_R$=387±15 $M^{-1}$; $K_S$=1136±78 $M^{-1}$.
Figure 16:
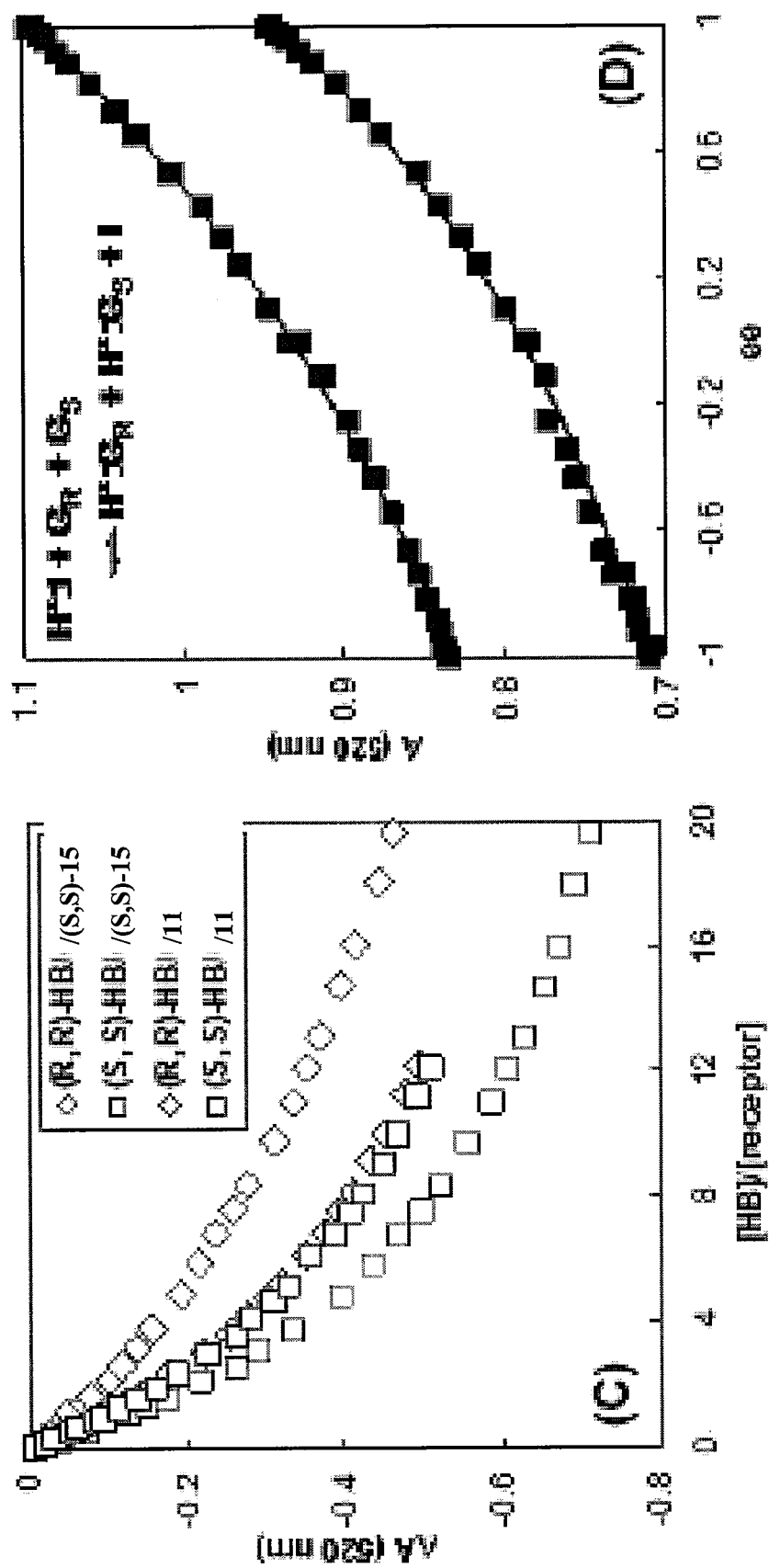

As an example, these empirical criteria were applied in the enantioselective binding studies between (S,S)-15 and HB. PV was again chosen as the indicator because of its weaker affinity—which was relatively close to that between HB and (S,S)-15. $[I]_t$ was set at 140 mM where the absorbance at 520 nm (the analyzed wavelength) was 1.7 when PV was saturated by the receptor (S,S)-15. In the displacement assays, an $[H]_t$ concentration (0.51 mM) was chosen to saturate the indicator at an 80% level at the inception. The absorbance at 520 nm decreased to different extents upon titration of the two enantiomers (FIGS. 16A and 16B). When the total analyte concentration ($[G]_t$) ranged from 4-15 mM, the chiral resolution of the enantioselective assay ($DA=|A_R-A_S|$) was almost constant at 0.25 (FIG. 16C). Therefore, this assay was optimized for an ee determination when an HB sample's total concentration was within 4-15 mM. The absorbance (A) vs. ee correlation is shown in FIG. 16D at two different concentrations ($[G]_t$). When $[G]_t=7.5$ mM, the red curve shows that the absorbance at 520 nm, where the bound indicator (H:I) absorbs, increases with the growing ee of (R,R)-HB ($ee_R$)—the weaker binding enantiomer. The absorbance change as a function of ee ($dA/dee_R$) increases as the $ee_R$ is getting larger (FIG. 16D). This is because the assay is more responsive to the change of stronger binding enantiomer concentration ($D[G]s$) when its concentration ($[G]s$) is relatively small than otherwise. When $[G]_t$ is increased to 15 mM, the overall absorption profile (blue) is around 0.12 absorbance units lower due to more competitive binding, while the other features remain. The assay responds to the change of $[G]_t$ and ee similarly to what was observed in the fluorescence studies, indicating that the assay's behavior reliably follows the laws governing solution multi-equilibria.

Seven data points were randomly selected from the two ee curves (FIG. 16D) as unknown samples. As described above, the curves were fit with the remaining data to determine values of $K_R$ and $K_S$. The ee values of the seven designated unknown HB samples were determined (Table 10) using a protocol similar to that with fluorimetry described in the previous section. The errors were within 10% of the actual values, except for the one data point that was at the least sensitive end of the ee curve. Similar failure at such data region was also observed in the fluorescence assay. The non-linear ee vs. A response originates from the different association of two enantiomeric compounds with one chiral receptor. In a future development, the enantiomeric receptor may need to be incorporated into the assay to compensate for the accuracy at the low sensitivity end of the ee curve.

TABLE 10

Determination of ees of 7 HB samples by spectrophotometry.

| | Sample No. | | | |
| --- | --- | --- | --- | --- |
| | 1 | 2 | 3 | 4 |
| Actual ee ($[G]_t = 7.5$ mM) | 0.92 | 0 | −0.98 | — |
| Determined ee | 0.85 | −0.09 | −1.09 | — |
| Actual ee ($[G]_t = 15$ mM) | 0.96 | 0.82 | 0 | −0.82 |
| Determined ee | 1.02 | 0.88 | 0.13 | −0.59 |

Figure 17:
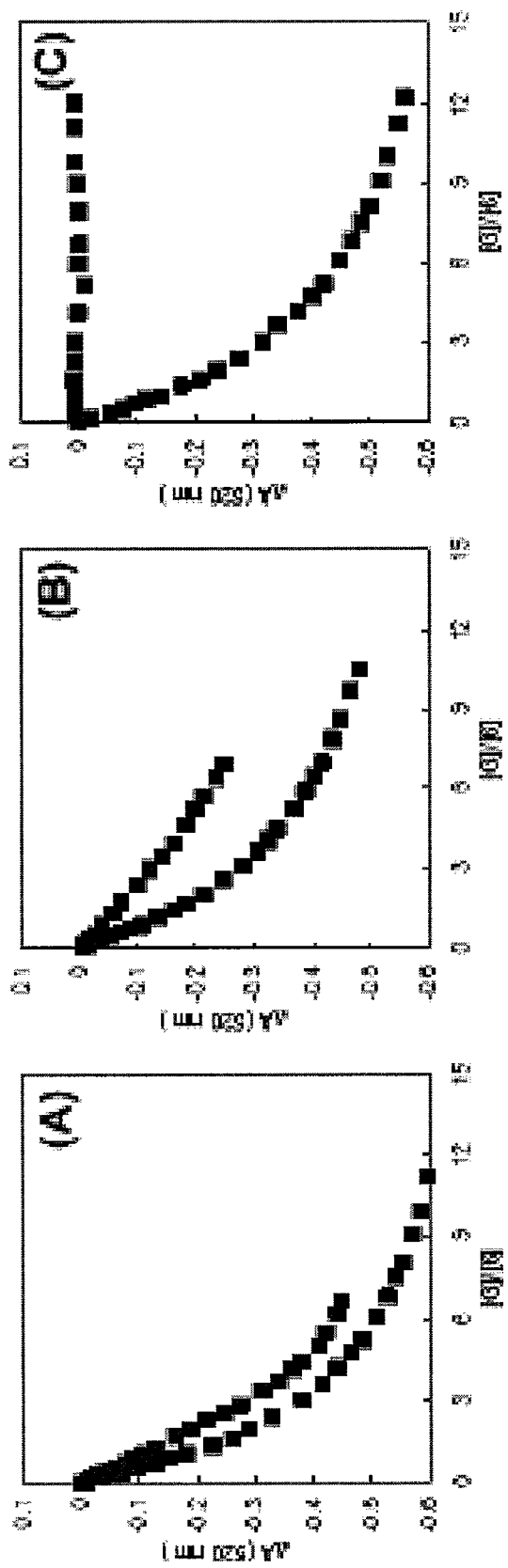
FIG. 17A illustrates the absorbance change at 520 nm of PV (149 mM) and receptor 11 (0.82 mM) in the default buffer (footnote, FIG. 12) with increasing concentrations of L-PL (blue) and PP (red); $K_{PP}$≈1.2 $10^3$ $M^{-1}$.
FIG. 17B illustrates the absorbance change at 520 nm of PV (149 mM) and receptor 6 (0.82 mM) in the default buffer with increasing concentrations of L-LC (blue) and PVA (red); $K_{LC}$=1.0 $10^3$ $M^{-1}$, $K_{PVA}$≈300 $M^{-1}$.
FIG. 17C illustrates the absorbance change at 520 nm of PV (149 mM) and receptor 6 (0.82 mM) in the default buffer with increasing concentrations of S-MD (blue) and BF (red). The association constants between pyruvic acids (PP and PVA) and 6 were estimated with the competitive spectrophotometric method, because their binding behaviors are also subject to processes other than solution equilibria.
Figure 18:
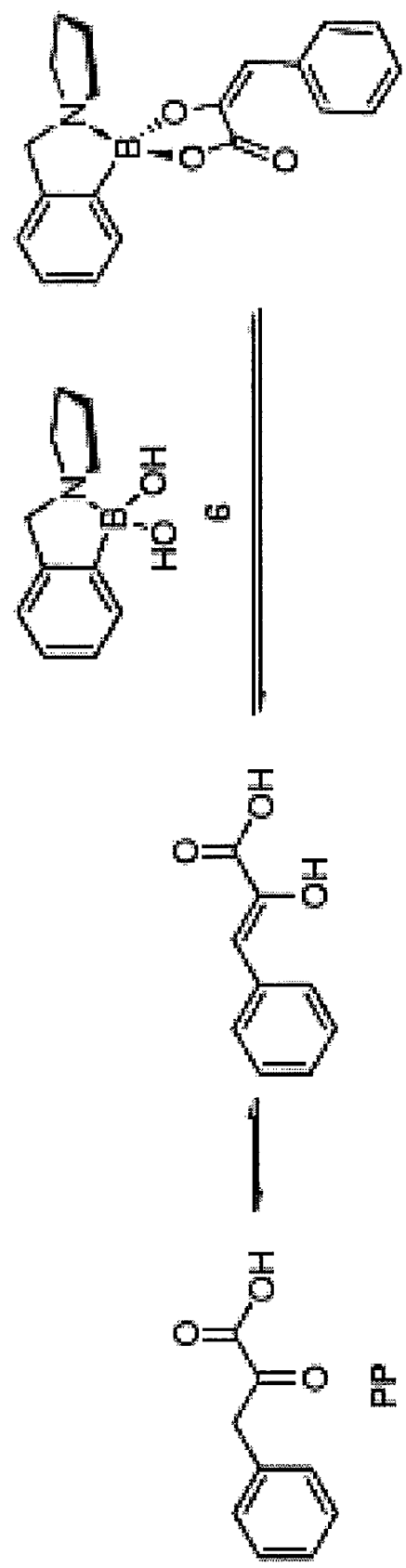
FIG. 18 illustrates the keto-enol tautomerization of phenyl pyruvic acid (PP) leads to its association with boronic receptors such as 6.

The affinities between three substituted pyruvates were also studied with indicator-displacement assays, because they are the synthetic precursors of a-hydroxycarboxylates through hydrogenation. Quite unexpectedly, substituted pyruvates bearing b-proton(s) bound with boronic acid receptors such as 11 with various strengths. Apparently the enol form of substituted pyruvates led to the formation of complexes (FIG. 18). As shown in FIG. 17A, PP and PL have comparable affinity to 11. The tautomerization of the keto form of PP affords an enolate structure that is stabilized through conjugation with the neighboring phenyl ring (FIG. 18), which leads to a strong association with receptor 11. Pyruvic acid (PVA), which lacks the extra stabilization for its enol form, displays less, albeit significant affinity to receptor 11 (FIG. 17B). Benzoyl formic acid (BF), which does not have b-protons and therefore is not able to tautomerize, does not associate with 11 (FIG. 17C).

Example 13

General Methods for ee Determination of α-Amino Acids

Reagents were obtained from Aldrich and used as received unless otherwise noted. Deionized water and A.C.S. spectroanalyzed methanol were used to prepare solutions for spectrophotometric titrations. A Varian Unity Plus 300 MHz spectrometer was used to obtain $^1H$ and $^{13}C$ NMR spectra which are referenced to the solvent. A Finnigan VG analytical ZAB2-E spectrometer was used to obtain high-resolution mass spectra. UV/vis spectra were recorded on a Beckman DU-640 spectrophotometer. All pH measurements were made using an Orion 720A pH meter.

Synthesis of (S,S)-22 by Reductive Amination.

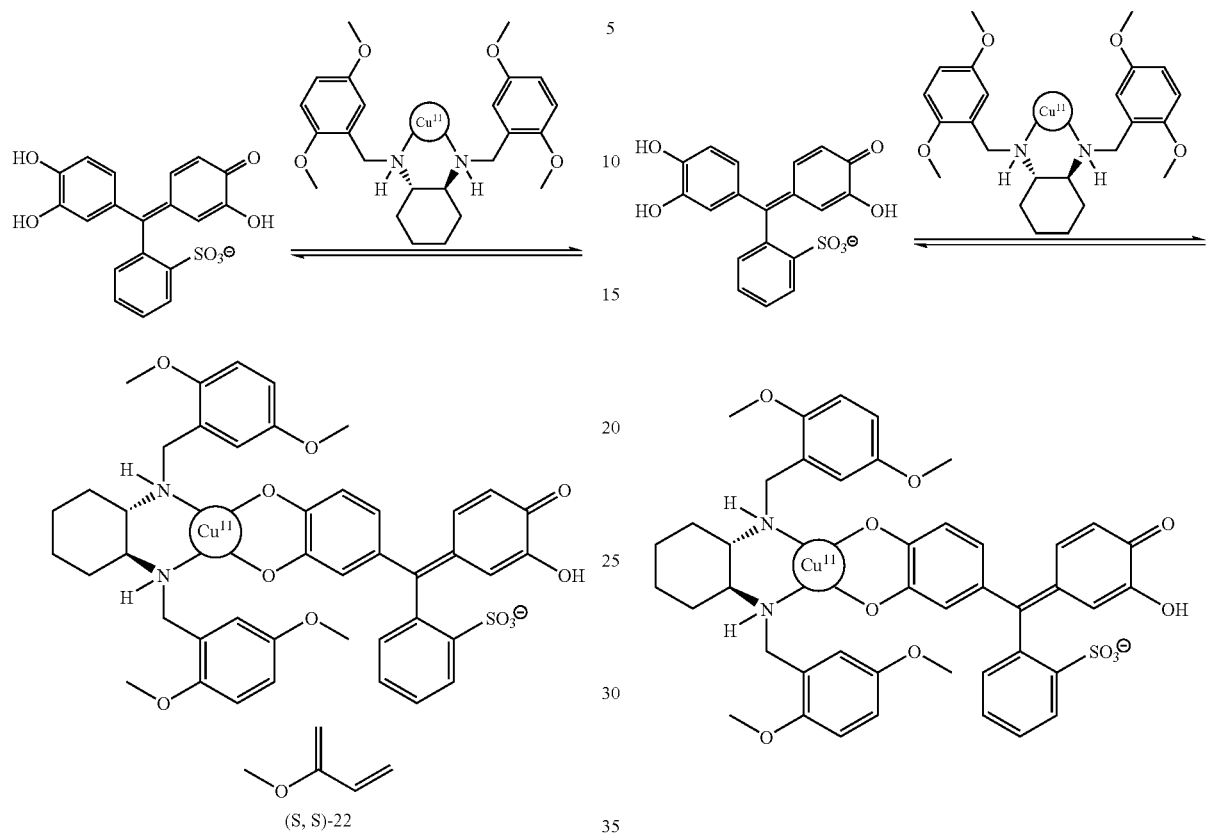

(S, S)-22

(S,S)-22: To a flame-dried 25 mL round bottom flask was added freshly distilled (S,S)-trans-diaminocyclohexane (300 mg, 2.63 mmol) and 2,5-dimethoxybenzaldehyde (835 mg, 5.03 mmol). These were dissolved in anhydrous MeOH (4 mL) and the solution was stirred under an argon atmosphere for 18 h at room temperature. After this time the solution was cooled to 0° C. and NaBH$_4$ (150 mg, 3.97 mmol) was added. After stirring for 1 h, a second portion of NaBH$_4$ (150 mg) was added. The reaction was stirred for an additional 1 h and concentrated under reduced pressure to give a white residue, which was taken up in CH$_2$Cl$_2$ (100 mL) and washed with 1 M NaOH$_{(aq)}$ (2·50 mL). The organic phase was then extracted with 1 M HCl$_{(aq)}$ (5·50 mL). The pH of the combined aqueous phase was adjusted by the addition of concentrated NaOH until basic by litmus and was extracted with CH$_2$Cl$_2$ (5·50 mL). The organic phase was then washed with brine (100 mL), dried over Na$_2$SO$_4$, filtered and concentrated to a colorless oil. (685 mg, 65% yield).

$^1$H NMR (CDCl$_3$)$^{tm}$ 6.900 (d, J=2.7 Hz, 2H), 6.731-6.714 (m, 4H), 3.867 (d, J=13.5 Hz 2H), 3.724 (s, 6H), 3.703 (s, 6H), 3.616 (d, J=13.5 Hz 2H), 2.252 (d, J=9.3 Hz, 2H), 2.133 (d, J=13.8 Hz, 2H), 2.002 (b, 2H), 1.223 (t, J=9.3 Hz, 2H), 1.073 (t, J=9.3 Hz, 2H); $^{13}$C NMR (CDCl$_3$)$^{tm}$ 153.7, 152.0, 130.6, 115.9, 112.2, 113.3, 61.1, 56.0, 55.9, 46.2, 31.7, 25.3; HRMS (CI, m/z) calcd for C$_{24}$H$_{34}$N$_2$O$_4$: 415.25966. Found: 415.25968.

Scheme S-23. The host-indicator association process monitored with S-22.

Scheme S-24. The indicator displacement process being monitored in Scheme S-23.

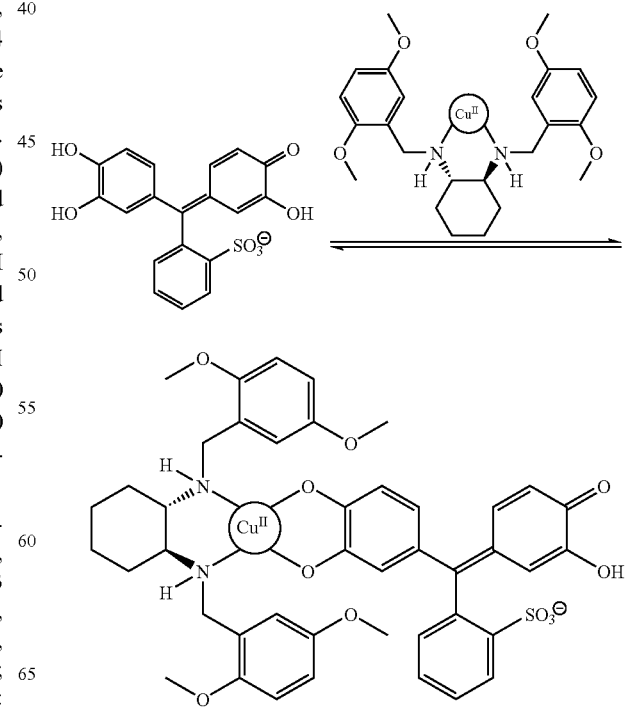

-continued

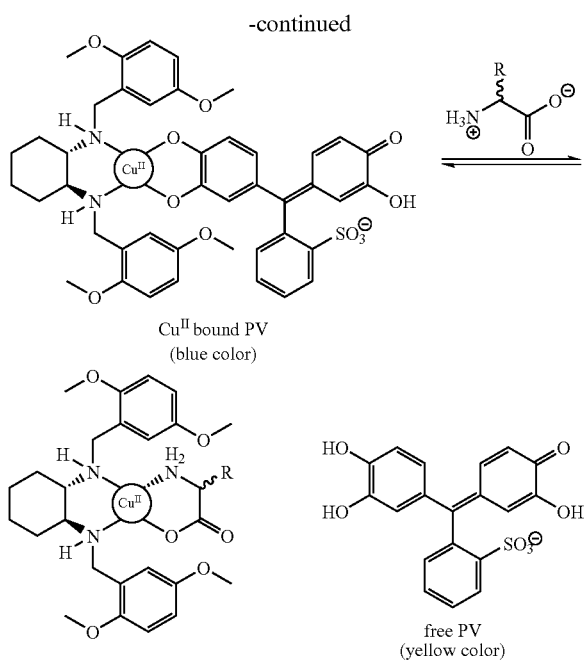

Cu<sup>II</sup> bound PV
(blue color)

free PV
(yellow color)

What is claimed is:

1. A method of determining in a solution enantiomeric excess of one enantiomer of a chiral analyte, said method comprising:
   adding a chiral receptor to the solution, the chiral receptor operable to bind different enantiomers of the analyte with differing affinities;
   adding an indicator that binds the chiral receptor, the indicator operable to change an optical property of the solution when displaced by the analyte;
   adding the analyte; and
   observing the optical property, the optical property upon displacement of the indicator by one enantiomer of the analyte being detectably different than the optical property upon displacement of the indicator by a different enantiomer of the analyte.

2. The method of claim 1, further comprising determining the enantiomeric excess of one enantiomer.

3. The method of claim 2, further comprising determining the enantiomeric excess through visual analysis.

4. The method of claim 2, further comprising determining the enantiomeric excess through spectrographic analysis.

5. The method of claim 4, further comprising determining the enantiomeric excess using an absorbance measurement through mathematical analysis.

6. The method of claim 1, further comprising determining the concentration of the analyte.

7. The method of claim 1, wherein the analyte comprises an α-hydroxyacid.

8. The method of claim 1, wherein the analyte comprises a molecule having pharmacological activity.

9. The method of claim 1, wherein the analyte comprises an amino acid.

10. The method of claim 1, wherein the indicator is selected from the group consisting of alizarin red S, alizarin complex one, 4-methylesculetin, pyrocatechol violet, and bromopyrogallol.

11. A method of screening drug candidates comprising:
    adding a chiral drug candidate;
    adding a chiral receptor to a solution, the chiral receptor operable to bind different enantiomers of the drug candidate with differing affinities;
    adding an indicator that binds the chiral receptor, the indicator operable to change an optical property of the solution when displaced by the drug candidate; and
    observing the optical property of the solution, the optical property observable upon displacement of the indicator by one enantiomer of the drug candidate being detectably different than the optical property observable upon displacement of the indicator by a different enantiomer of the drug candidate,
    wherein the optical property observed indicates whether the drug candidate meets governmental regulations.

12. The method of claim 11, wherein the governmental regulations comprise FDA regulations.

* * * * *

UNITED STATES PATENT AND TRADEMARK OFFICE
CERTIFICATE OF CORRECTION

PATENT NO.       : 7,670,847 B2                                               Page 1 of 1
APPLICATION NO.  : 11/839085
DATED            : March 2, 2010
INVENTOR(S)      : Anslyn et al.

It is certified that error appears in the above-identified patent and that said Letters Patent is hereby corrected as shown below:

Please amend the Statement of Government Interest of the patent as follows:

~~The present invention or aspects thereof were invented in whole or in part using funding provided by the National Institutes of Health, Grant GM57306. The U.S. Government may have certain rights in the invention.~~

Col. 1 lines 15-18 should read,

This invention was made with government support under GM57306 awarded by the National Institutes of Health. The Government has certain rights in the invention.

Signed and Sealed this

Fourteenth Day of December, 2010

David J. Kappos
*Director of the United States Patent and Trademark Office*